US011594066B2

(12) United States Patent
Ogirko et al.

(10) Patent No.: US 11,594,066 B2
(45) Date of Patent: *Feb. 28, 2023

(54) SENSOR-COMPATIBLE OVERLAY

(71) Applicant: Cypress Semiconductor Corporation, San Jose, CA (US)

(72) Inventors: Roman Ogirko, Lviv (UA); Hans Klein, Pleasanton, CA (US); David G. Wright, San Mateo, CA (US); Igor Kolych, Lviv (UA); Andriy Maharyta, Lviv (UA); Hassane El-Khoury, Pleasanton, CA (US); Oleksandr Karpin, Lviv (UA); Oleksandr Hoshtanar, Lviv (UA); Igor Kravets, Lviv (UA)

(73) Assignee: Cypress Semiconductor Corporation, San Jose, CA (US)

( * ) Notice: Subject to any disclaimer, the term of this patent is extended or adjusted under 35 U.S.C. 154(b) by 308 days.

This patent is subject to a terminal disclaimer.

(21) Appl. No.: 17/078,037

(22) Filed: Oct. 22, 2020

(65) Prior Publication Data

US 2021/0150180 A1 May 20, 2021

Related U.S. Application Data

(63) Continuation of application No. 16/365,994, filed on Mar. 27, 2019, now Pat. No. 10,832,029, which is a (Continued)

(51) Int. Cl.
*G06V 40/13* (2022.01)
*A61B 46/10* (2016.01)
(Continued)

(52) U.S. Cl.
CPC .......... *G06V 40/1329* (2022.01); *A61B 42/10* (2016.02); *A61B 42/20* (2016.02);
(Continued)

(58) Field of Classification Search
CPC ............ G06V 40/1306; G06V 40/1329; H01S 3/022; H01S 3/092; H01S 3/1312;
(Continued)

(56) References Cited

U.S. PATENT DOCUMENTS

2010/0113952 A1 5/2010 Raguin et al.
2015/0189136 A1* 7/2015 Chung ................... G06V 40/13
348/77

FOREIGN PATENT DOCUMENTS

CN 1278347 A 12/2000
CN 104932763 A 9/2015
(Continued)

*Primary Examiner* — Manuchehr Rahmjoo

(57) ABSTRACT

A fingerprint sensor-compatible overlay material which uses anisotropic conductive material to enable accurate imaging of a fingerprint through an overlay is disclosed. The anisotropic conductive material has increased conductivity in a direction orthogonal to the fingerprint sensor, increasing the capacitive coupling of the fingerprint to the sensor surface, allowing the fingerprint sensor to accurately image the fingerprint through the overlay. Methods for forming a fingerprint sensor-compatible overlay are also disclosed.

16 Claims, 28 Drawing Sheets

Related U.S. Application Data continuation of application No. 16/113,374, filed on Aug. 27, 2018, now Pat. No. 10,282,585, which is a continuation-in-part of application No. 15/472,473, filed on Mar. 29, 2017, now Pat. No. 10,235,558, and a continuation-in-part of application No. 15/368,905, filed on Dec. 5, 2016, now Pat. No. 10,061,961, said application No. 15/472,473 is a continuation of application No. 15/347,400, filed on Nov. 9, 2016, now Pat. No. 9,639,734, said application No. 15/368,905 is a continuation of application No. 15/088,479, filed on Apr. 1, 2016, now Pat. No. 9,547,788.

(60) Provisional application No. 62/316,451, filed on Mar. 31, 2016, provisional application No. 62/255,220, filed on Nov. 13, 2015, provisional application No. 62/255,027, filed on Nov. 13, 2015.

(51) Int. Cl.

| | |
|---|---|
| *A61B 42/10* | (2016.01) |
| *A61B 42/20* | (2016.01) |
| *H01S 3/213* | (2006.01) |
| *A61B 18/00* | (2006.01) |
| *H01S 3/131* | (2006.01) |
| *A61B 17/00* | (2006.01) |
| *A61B 18/20* | (2006.01) |
| *H01S 3/02* | (2006.01) |
| *H01S 3/092* | (2006.01) |

(52) U.S. Cl.
CPC .......... *A61B 46/10* (2016.02); *G06V 40/1306* (2022.01); *A61B 18/20* (2013.01); *A61B 18/203* (2013.01); *A61B 2017/00057* (2013.01); *A61B 2018/00452* (2013.01); *A61B 2018/00476* (2013.01); *H01S 3/022* (2013.01); *H01S 3/092* (2013.01); *H01S 3/1312* (2013.01); *H01S 3/213* (2013.01)

(58) Field of Classification Search
CPC ....... H01S 3/213; A61B 18/20; A61B 18/203; A61B 2017/00057; A61B 2018/00452; A61B 2018/00476; A61B 42/10; A61B 42/20; A61B 46/10
See application file for complete search history.

(56) References Cited

FOREIGN PATENT DOCUMENTS

| NL | 2010812 A | 11/2013 |
|---|---|---|
| WO | 9852145 A1 | 11/1998 |
| WO | 0169520 A2 | 9/2001 |

* cited by examiner

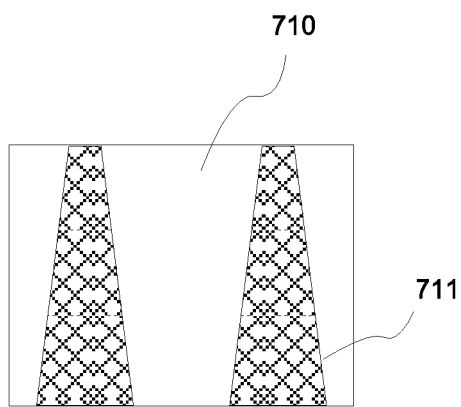 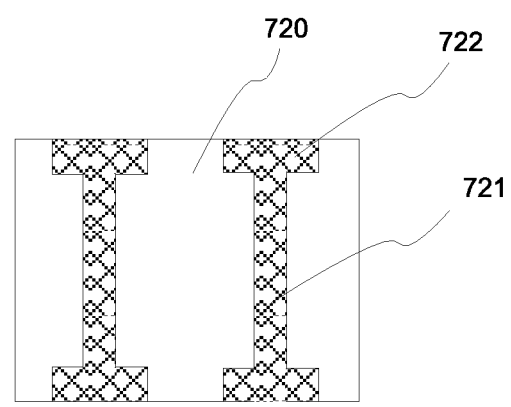
FIGURE 7A  FIGURE 7B

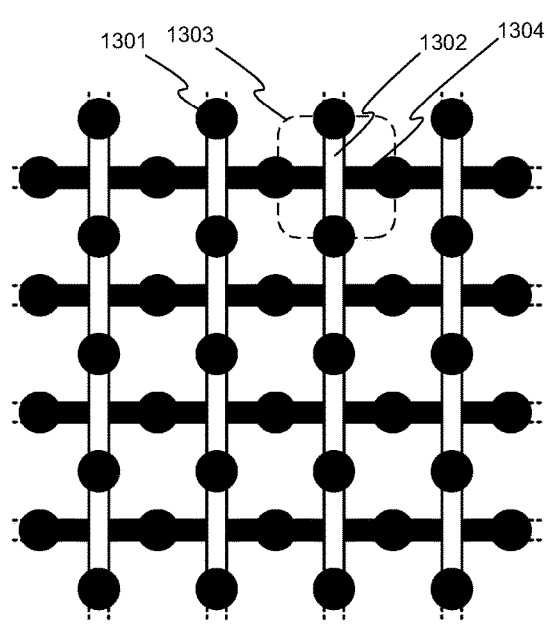
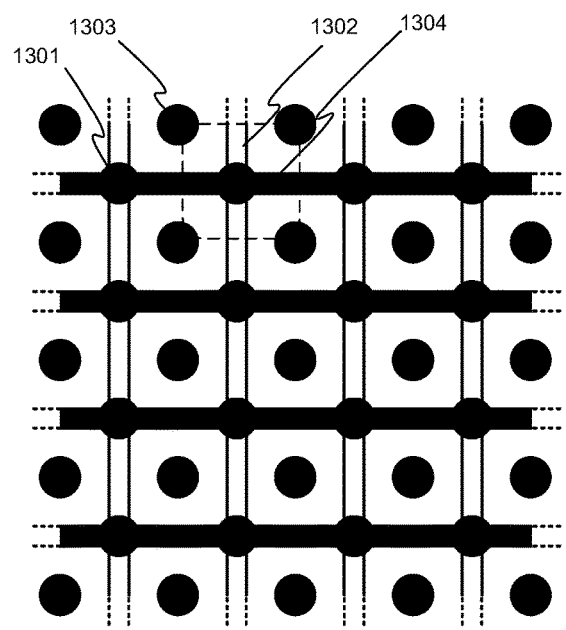
Figure 13E
Figure 13F

FIGURE 15A FIGURE 15B

SENSOR-COMPATIBLE OVERLAY

RELATED APPLICATIONS

The present application is a continuation of U.S. patent application Ser. No. 16/365,994 filed on Mar. 27, 2019, which is a continuation of U.S. patent application Ser. No. 16/113,374, filed Aug. 27, 2018, which issued as U.S. Pat. No. 10,282,585 on May 7, 2019, which is a continuation-in-part of U.S. patent application Ser. No. 15/472,473, filed Mar. 29, 2017, which issued as U.S. Pat. No. 10,235,558 on Mar. 19, 2019, which is a continuation of U.S. patent application Ser. No. 15/347,400, filed Nov. 9, 2016, which issued as U.S. Pat. No. 9,639,734 on May 2, 2017 and claims priority to U.S. Provisional Patent Application Nos. 62/255,027, filed Nov. 13, 2015 and 62/316,451, filed Mar. 31, 2016, and this application is a continuation-in-part of U.S. patent application Ser. No. 15/368,905, which was filed Dec. 5, 2016, which issued as U.S. Pat. No. 10,061,961 on Aug. 28, 2018, and is a continuation of U.S. patent application Ser. No. 15/088,479, which filed Apr. 1, 2016 and issued as U.S. Pat. No. 9,547,788 on Jan. 17, 2017 and claim the benefit of U.S. Provisional Patent Application No. 62/255,220, filed Nov. 13, 2015, all of which is incorporated by reference herein in its entirety.

TECHNICAL FIELD

The present disclosure relates generally to fingerprint sensing, and more particularly to the sensing of a fingerprint through an overlay material.

BACKGROUND

Various devices and systems such as computing devices (e.g., notebook computers, tablets, personal digital assistants, smartwatches, mapping devices, audio players), mobile communication devices (e.g., smartphones, cellphones), automotive equipment (e.g., cars, trucks, motorcycles), industrial equipment (e.g., machinery, tools), home white goods (e.g., appliances, security systems), and entry systems (e.g., home entry, automotive entry, secure area entry) may require an authentication method to protect against unauthorized access. Fingerprint authentication using fingerprint sensors may protect an apparatus or system against unauthorized access.

Fingerprint sensors may use various capacitive sensing methods to image a fingerprint pattern, where imaging a fingerprint means detecting a fingerprint and generating a set of data values, or "fingerprint data," that represents the fingerprint in digital format. The fingerprint data may be an image or other information specific to a fingerprint. This method requires direct contact or close proximity of the portion of the finger comprising the fingerprint, or "finger pad," with the sensor surface. A very thin cover, or overlay, may be disposed over the sensor surface. Overlays may typically be less than 150 µm in thickness. Thick covers or overlays between the fingerprint and the fingerprint sensor may obscure fingerprint features.

There may be a variety of situations when a user wearing a glove or other hand enclosure may want to image a fingerprint. A glove may protect the hand against harmful environmental factors, such as cold and water, and harmful physical factors, such as sharp objects and corrosive chemicals. A glove may be fabricated using material such as, but not limited to, fabric, latex, or rubber. Current fingerprint sensors cannot image fingerprints through glove materials. Using glove materials that are thin enough to enable fingerprint sensing may limit the protective effectiveness of the materials. If using thick glove materials, the user may have to remove the glove to image a fingerprint, which may be inconvenient and/or dangerous. It is desirable to create a glove or other hand enclosure using materials that are thick enough for protection but enable a fingerprint sensor to accurately image a fingerprint.

Similarly, devices with fingerprint sensors are often enclosed in a protective enclosure, or the front face of the device is covered by a protective cover. A protective enclosure or cover protects the device and/or sensor against harmful environmental factors, such as cold and water, and harmful physical factors, such as sharp objects and corrosive chemicals. A protective enclosure or cover may be fabricated with rigid material, such as, but not limited to, glass or plastic, or flexible material, such as, but not limited to, fabric or film. A protective enclosure may completely enclose a device or may partially enclose a device. Current fingerprint sensors cannot image fingerprints through thick material. Using an enclosure or cover material that is thin enough to enable fingerprint sensing may limit the protective effectiveness of the enclosure or film. If using a thick enclosure or cover material, the user may have to remove the device from the enclosure or cover to enable fingerprint sensing. Removing the cover or enclosure may be inconvenient for the user and and/or may risk damaging the device. It is desirable to create a protective enclosure or cover made of material that is thick enough for protection but enables a fingerprint sensor to accurately image a fingerprint.

SUMMARY

In an embodiment, a method is disclosed for constructing using material that is thick enough for protection but enables a fingerprint sensor to accurately image a fingerprint through the overlay. The method includes incorporating an anisotropic conductive material into the portion of the overlay disposed over the fingerprint sensor. The anisotropic conductive material is substantially more conductive in one direction, such as a direction orthogonal to the surface of a fingerprint sensor, than in other directions, increasing the capacitive coupling of the fingerprint to the sensor surface, allowing the fingerprint sensor to accurately image the fingerprint.

In an embodiment, a method is disclosed for constructing a protective enclosure or cover using material that is thick enough for protection but enables a fingerprint sensor to accurately image a fingerprint without removing the protective enclosure or cover. The method includes incorporating an anisotropic conductive material into the portion of the protective enclosure or cover disposed over the fingerprint sensor. The anisotropic conductive material is substantially more conductive in one direction, such as a direction orthogonal to the surface of a fingerprint sensor, than in other directions, increasing the capacitive coupling of the fingerprint to the sensor surface, allowing the fingerprint sensor to accurately image the fingerprint.

In an embodiment, a method is disclosed for constructing a glove or other hand enclosure using material that is thick enough for protection but enables a fingerprint sensor to accurately image a fingerprint without taking off the glove or hand enclosure. The method includes incorporating an anisotropic conductive material into a fingertip area of a glove or hand enclosure. The anisotropic conductive material is substantially more conductive in a direction orthogonal to the surface of a finger pad, increasing the capacitive coupling of the fingerprint to the sensor surface, allowing the fingerprint sensor to accurately image the fingerprint.

In an embodiment, an overlay is disclosed. The overlay incorporates an anisotropic conductive material into a portion of the overlay disposed over a fingerprint sensor. The anisotropic conductive material is substantially more conductive in a direction orthogonal to the surface of a fingerprint sensor, increasing the capacitive coupling of the fingerprint to the sensor surface, allowing the fingerprint sensor to accurately image the fingerprint.

In an embodiment, a protective enclosure or cover is disclosed. The enclosure or cover incorporates an anisotropic conductive material into a portion of the protective enclosure or cover disposed over a fingerprint sensor. The anisotropic conductive material is substantially more conductive in a direction orthogonal to the surface of a fingerprint sensor, increasing the capacitive coupling of the fingerprint to the sensor surface, allowing the fingerprint sensor to accurately image the fingerprint.

In an embodiment, a glove or other hand enclosure is disclosed. The glove or hand enclosure incorporates an anisotropic conductive material into a fingertip area of the glove or hand enclosure. The anisotropic conductive material is substantially more conductive in a direction orthogonal to the surface of a finger pad, increasing the capacitive coupling of the fingerprint to the sensor surface, allowing the fingerprint sensor to accurately image the fingerprint.

In an embodiment, an anisotropic conductive material is disclosed which is thick enough for protection but enables a fingerprint sensor to accurately image a fingerprint through the material. The anisotropic conductive material is substantially more conductive in one direction, such as a direction orthogonal to the surface of a fingerprint sensor, than in other directions, increasing the capacitive coupling of the fingerprint to the sensor surface, allowing the fingerprint sensor to accurately image the fingerprint through the material.

In an embodiment, method for fabricating an anisotropic conductive material is disclosed. The anisotropic conductive material is substantially more conductive in one direction, than in other directions.

In an embodiment, a method is disclosed for imaging a fingerprint by a fingerprint sensor overlayed with an anisotropic conductive material which is thick enough to provide protection but enables the fingerprint sensor to accurately image a fingerprint through the material. The anisotropic conductive material is substantially more conductive in one direction, such as a direction orthogonal to the surface of a fingerprint sensor, than in other directions, increasing the capacitive coupling of the fingerprint to the sensor surface, allowing the fingerprint sensor to accurately image the fingerprint through the material.

In an embodiment, a fingerprint sensor apparatus is disclosed for imaging a fingerprint by a fingerprint sensor overlayed with an anisotropic conductive material which is thick enough to provide protection but enables the fingerprint sensor to accurately image a fingerprint through the material. The anisotropic conductive material is substantially more conductive in one direction, such as a direction orthogonal to the surface of a fingerprint sensor, than in other directions, increasing the capacitive coupling of the fingerprint to the sensor surface, allowing the fingerprint sensor to accurately image the fingerprint through the material.

DESCRIPTION OF THE DRAWINGS

FIGS. 7A-7B illustrate a material with pillars fabricated in the material in shapes according to various embodiments.

FIGS. 13A-13I illustrate arrangements of pillars according to various embodiments.

DETAILED DESCRIPTION

Figure 1:
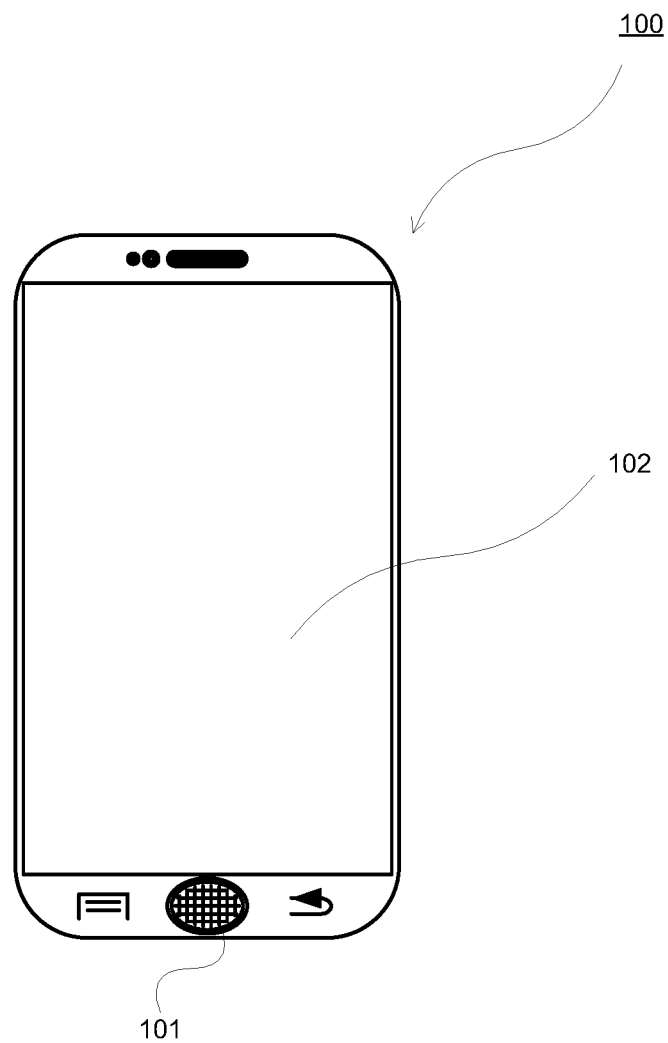
FIG. 1 illustrates a device with a fingerprint-enabled authentication system.

In the following description, for purposes of explanation, numerous specific details are set forth in order to provide a thorough understanding of the embodiments of the present invention discussed herein. It will be evident, however, to one skilled in the art that these and other embodiments may be practiced without these specific details. In other instances, well-known circuits, structures, and techniques are not shown in detail, but rather in a block diagram in order to avoid unnecessarily obscuring an understanding of this description.

Reference in the description to "one embodiment" or "an embodiment" means that a particular feature, structure, or characteristic described in connection with the embodiment is included in at least one embodiment of the invention. The phrase "in one embodiment" located in various places in this description does not necessarily refer to the same embodiment.

For simplicity and clarity of illustration, reference numerals may be repeated among the figures to indicate corresponding or analogous elements. Numerous details are set forth to provide an understanding of the embodiments described herein. The examples may be practiced without these details. In other instances, well-known methods, procedures, and components are not described in detail to avoid obscuring the examples described. The description is not to be considered as limited to the scope of the examples described herein.

Fingerprint Sensing and Imaging

FIG. 1 illustrates an embodiment of a device 100 with a fingerprint-enabled authentication system. Device 100 may be a mobile communication device such as a smartphone, cellphone, or tablet, comprising a fingerprint sensor 101 which may enable user access to device applications. In other embodiments, device 100 may be a key fob or remote control. Surface 102 may be a display or touchscreen. Device 100 is shown as a wireless communication device (e.g. a mobile phone), but this is not intended to be limiting. Rather, handheld devices that require fingerprint security may take various forms and have various uses. Other embodiments of devices or systems system with a fingerprint-enabled authentication systems may include an automotive console comprising a fingerprint sensor to enable the user to start the engine, an industrial control pad comprising a fingerprint sensor which may enable the user to operate the equipment, a home security console comprising a fingerprint sensor which may enable the user to arm or disarm the system, an entry pad comprising a fingerprint sensor which may enable a user to enter a secure area, and an automotive door entry pad comprising a fingerprint sensor which may enable the user to lock or unlock the automobile.

In each such device or system, a fingerprint may be imaged using a fingerprint sensor 101, where imaging a fingerprint may comprise detecting a fingerprint and generating a set of data values, or "fingerprint data," that represents the fingerprint in digital format. The fingerprint data may then be stored in a memory location. A second fingerprint may subsequently be imaged. The first set and second set of fingerprint data may be compared to determine if they share fingerprint features. Upon determining the two sets of fingerprint data share a significant number of features, the device may enable the user to access the device or system.

Fingerprint sensors may comprise a capacitive fingerprint sensor array. A capacitive fingerprint sensor array refers to a sensor array that includes capacitive sense elements that may produce signals suitable for detecting, determining positions of, tracking, and/or imaging the features of the fingerprint on or near a sensing surface. A capacitive sense element may comprise an electrode, a discrete unit of electrodes, or an intersection of electrodes from which a measurement or signal may be obtained that is separate and distinct from measurements/signals obtained from other sense elements in the capacitive sensor array. A unit cell refers to a discrete area of the capacitive sensor array in which every point within the unit cell is closer to one sense element than to an adjacent sense element.

Capacitive fingerprint sensors function by measuring the capacitance of a capacitive sense element and detecting a change in capacitance indicating a presence or absence of fingerprint features. Fingerprint features may include, but are not be limited to, valleys and ridges forming arches, loops, and whorls. For example, when a fingerprint ridge comes into contact with or is in close proximity to a sense element, the capacitance change caused by the fingerprint ridge may be detected. The capacitance change of the sense elements may be measured by electrical circuitry that converts the capacitances measured from the capacitive sense elements into digital values from which fingerprint data may be derived. As used herein, "fingerprint data" refers to a set of data values that represent a fingerprint in digital format. In some embodiments, fingerprint data may be a dataset that visually represents the valleys and ridges of a fingerprint with their arches, loops, and whorls. In other embodiments, fingerprint data may digitally represent a fingerprint in a non-visual form.

Figure 2:
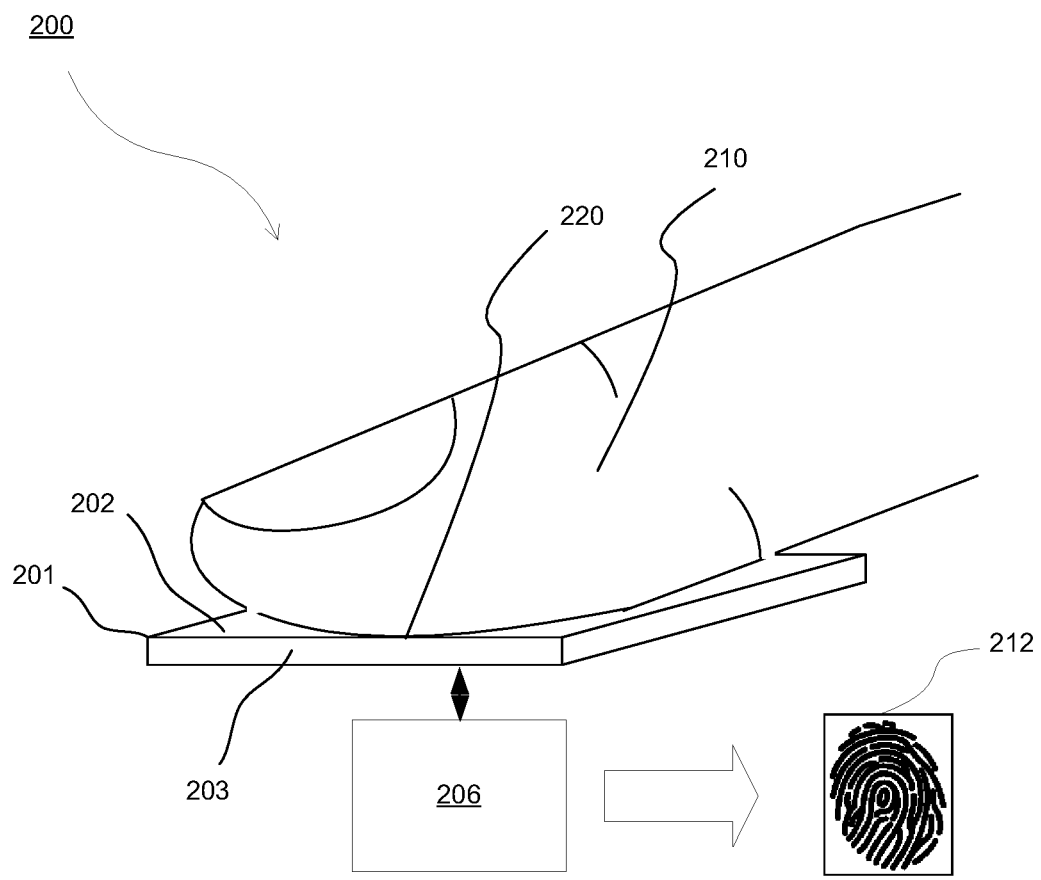
FIG. 2 illustrates a fingerprint sensing system.

FIG. 2 illustrates a fingerprint sensing system 200 in accordance with various embodiments. The fingerprint sensing system 200 includes a fingerprint sensor 201 and a fingerprint controller 206. Fingerprint sensor 201 may include a surface 202. A portion of finger 210 comprising a fingerprint, or "finger pad," 220 may be disposed on or in close proximity to surface 202. Fingerprint sensor 201 comprises an array of capacitive sensors 203 (not shown). Surface 202 may be disposed over array 203, which experiences changes in capacitance in response to the contact or proximity of fingerprint features of finger 210. Surface 202 may protect the capacitive sense elements from damage caused by direct physical contact by finger 210 or other objects. Surface 202 may also protect capacitive sense elements 203 from harmful environmental factors, such as cold or water, and harmful physical factors, such as impacts, projectile objects, and corrosive chemicals. Fingerprint sensor 201 and/or sensor surface 202 may be in the shape of a square, rectangle, circle, or any other shape. Fingerprint sensor 201 may be coupled to controller 206. Controller 206 may be configured to receive voltage or current signals measured by capacitive sense elements 203 which correspond to measured capacitance on and/or between capacitive sense elements 203, and to convert the voltage or current signals to fingerprint data, represented by visual representation of a fingerprint 212.

Figure 3:
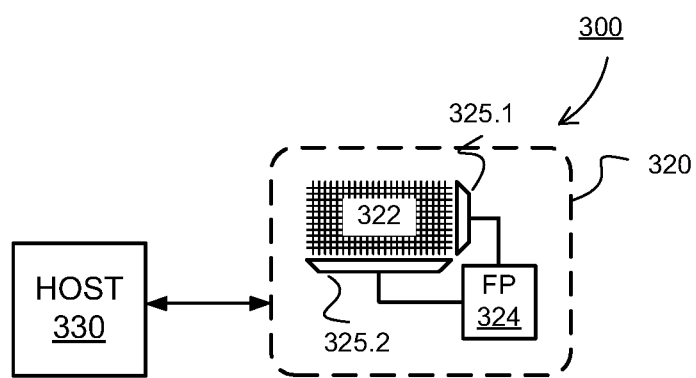
FIG. 3 illustrates a system that includes a fingerprint imaging module.

FIG. 3 illustrates an embodiment of a system 300 that includes a fingerprint imaging module 320. Fingerprint imaging module 320 may include an array 322 of capacitive sense elements (203 of FIG. 2) that are disposed in a location accessible to a user's finger. Array 322 may be disposed beneath a cover layer corresponding to surface 202 of FIG. 2. The capacitive sense elements 203 of array 322 may be coupled to a fingerprint controller 324 through multiplexors 325.1 and 325.2. Fingerprint controller 324 may be configured to receive voltage or current signals measured by sense elements (203 of FIG. 2) of array 322 which correspond to measured capacitance on and/or between electrodes of sense elements (203 of FIG. 2), and convert the voltage or current signals into fingerprint data. Fingerprint data may then be passed to host 330 for further processing, to store the fingerprint data in a library, or to compare the fingerprint data to one of a library of stored fingerprint data corresponding to one or more fingerprint images. The library of stored fingerprint data may be stored in a memory, which may be integrated with fingerprint controller 324, host 330, or as a separate circuit element (not shown).

In various embodiments, portions of system 300 may be integrated into different devices. For example, in an embodiment, sensor array 322, fingerprint controller 324 and host 330 may be on the same integrated circuit. In another embodiment, sensor array 322 may be on one integrated circuit and the detection and imaging portions (logic) of each controller may be on separate integrated circuits. All the digital processing may be executed on a single controller, such as the host, or, in other embodiments, the processing may be distributed to different controllers in the system.

Figure 4:
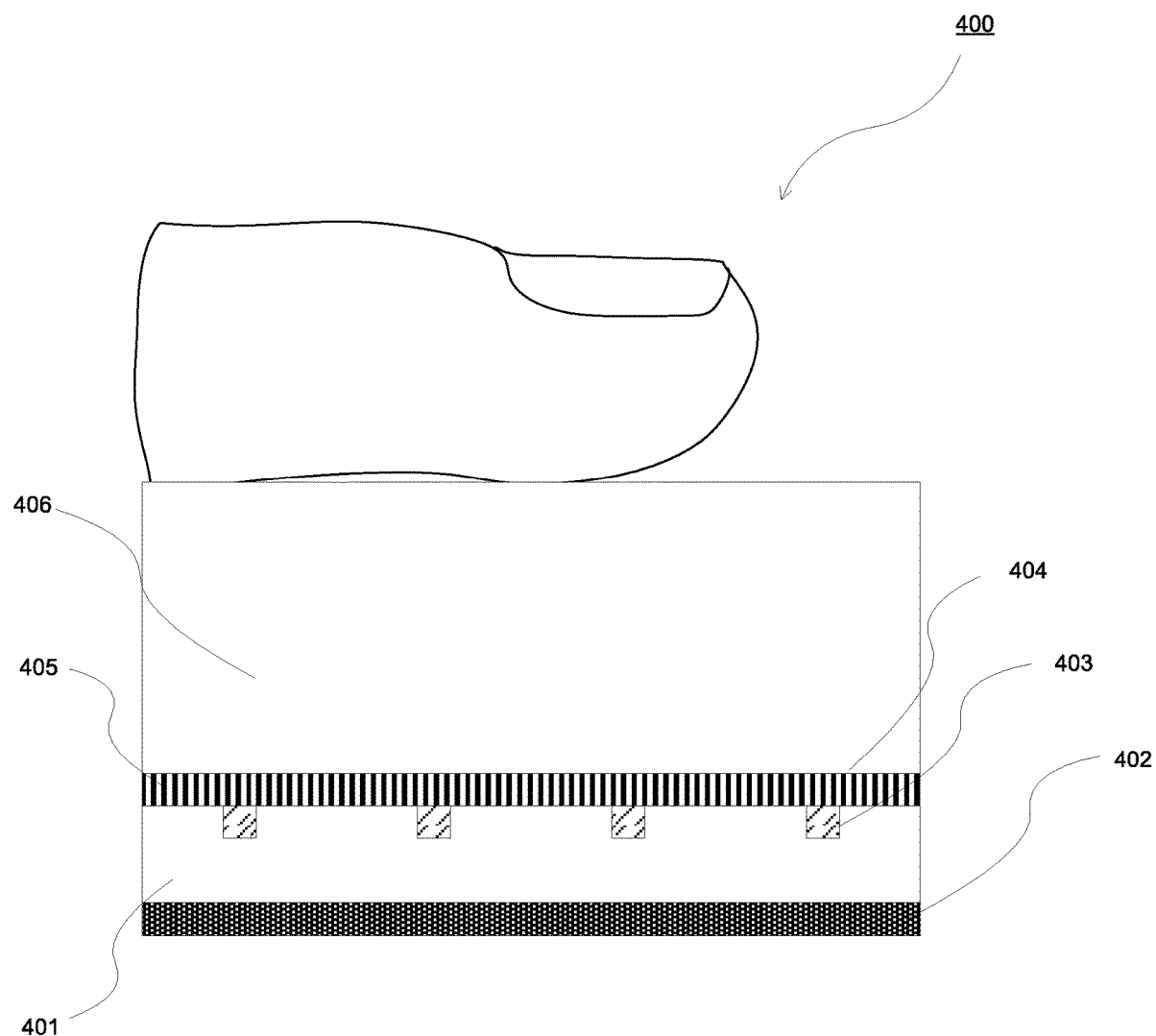
FIG. 4 illustrates a fingerprint sensor structure.

FIG. 4 illustrates a fingerprint sensor structure 400 in accordance with various embodiments. The fingerprint sensor structure 400 includes a fingerprint sensor 401, which includes a sensor array comprising Tx electrodes 402 and Rx electrodes 403, and a sensor surface 404. Fingerprint sensor structure 400 includes an overlay 406 and an intermediate layer 405, which may be glass to provide a sensor surface, or adhesive to attach overlay 406, or paint for color matching. In other embodiments there may be more than one intermediate layer between sensor surface 404 and overlay 406, or between overlay 406 and fingerprint pad 407.

Figure 5:
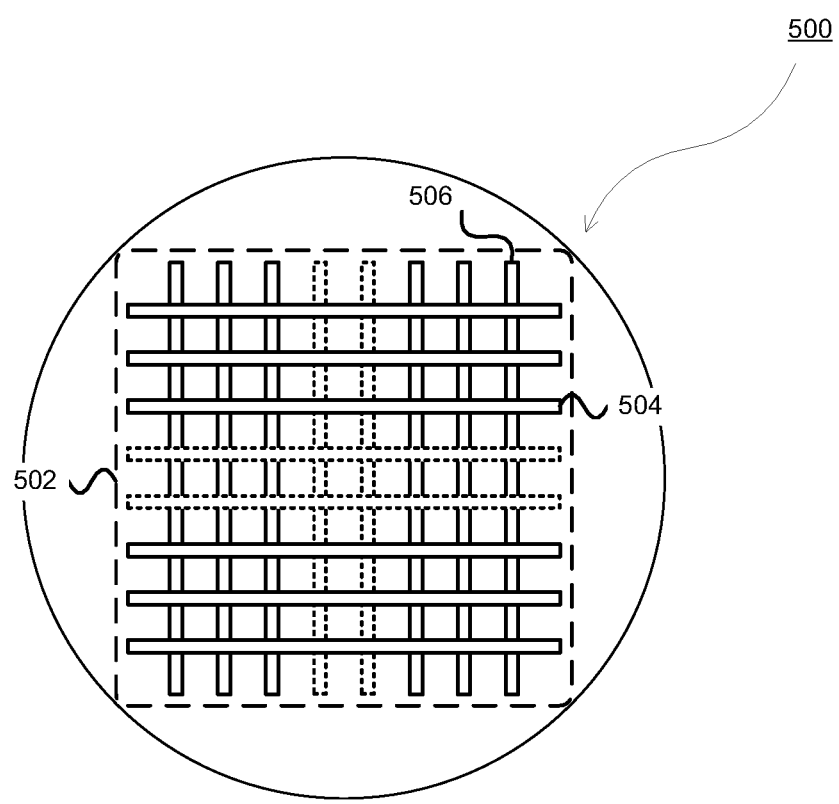
FIG. 5 illustrates a capacitive sensor array suitable for detecting and imaging fingerprints.

FIG. 5 illustrates an embodiment of a capacitive sensor array 500 suitable for detecting and imaging fingerprints. Capacitive sensor array 500 may include a number of electrodes arranged in an array 502 of row electrodes 504 in a first axis and column electrodes 506 in a second axis. FIG. 5 illustrates eight row electrodes 504 and eight column electrodes 506, but there may be considerably more electrodes disposed along both axes. Depending on the size of the array, there may be dozens or hundreds of electrodes for each row and column. The exact size and pitch of the electrodes may depend on the system design requirements.

A fingerprint sensor system as illustrated in FIGS. 2-5 may include certain features to enable accurate imaging of a fingerprint. In an embodiment, the pitch of row electrodes and column electrodes may be small enough such that multiple rows or columns may be disposed within a valley or along a ridge of a fingerprint feature when a finger is in contact with, or in close proximity to, a fingerprint sensor surface. In some embodiments, the pitch may be selected such that each fingerprint feature may be detected by a minimum number of capacitive sense elements (e.g., at least three capacitive sense elements). In various embodiments, the pitch of the capacitive sense elements may be less than 100 μm.

In an embodiment, the sensor surface of the fingerprint sensor may be a size that allows imaging of an adequate number of fingerprint features to allow differentiation between one fingerprint and another. In various embodiments, the area of the sensor surface of the fingerprint sensor may be in the range from 4×4 mm to 12×12 mm.

The thickness of the fingerprint sensor surface, or the thickness of an overlay disposed over the sensor surface, may affect the change in measured capacitance of a capacitive sense element in response to a proximate fingerprint feature. The change in capacitance that may be measured in response to a fingerprint feature is around 0.05 fF. For example, a thick sensor surface or overlay may reduce the change in measured capacitance of a capacitive sense element in response to a proximate fingerprint feature, which may obscure the fingerprint details.

Anisotropic Conductive Material

The sensor surface of a capacitive fingerprint sensor, or an overlay disposed on the sensor surface, may typically be made of an isotropic conductive material. In other words, the conductivity of the material is substantially the same in all directions. In an embodiment, the sensor surface or overlay may be made of an anisotropic conductive material. Anisotropic conductive material may be substantially more conductive in one direction, such as a direction orthogonal to a fingerprint sensor surface, than in other directions.

One method of fabricating anisotropic conductive material may to fabricate conductive pathways, or "pillars," in a material.

Figure 6A:
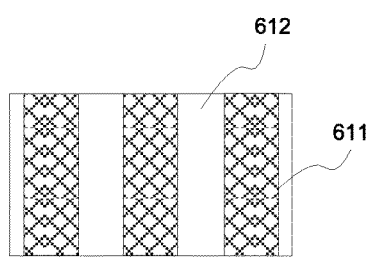
FIGS. 6A-6C illustrate a material with pillars that are fabricated in the material in one direction according to various embodiments.

FIGS. 6A-5C illustrate one method of fabricating anisotropic conductive material by fabricating conductive pathways, or "pillars," in a material. Pillars may be fabricated by methods including, but not limited to, drilling, piercing, or perforating a material, including laser-assisted methods. The pillars may be areas within the material that are devoid of the material. The pillars may be fully or partially filled with air, dielectric material, or a conductive material. Pillars may be filled with material by methods including, but not limited to, pasting material in the pillars, electro-plating the pillars, or depositing micro-particles. The pillars may be fully or partially filled. The pillars may be coated with a conductive material. The conductive material may comprise copper or indium tin oxide (ITO).

Figure 6B:
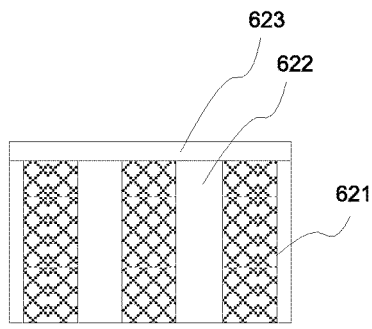
Figure 6C:
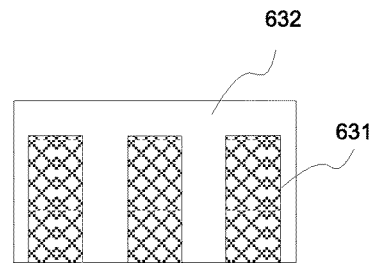

FIG. 6A illustrates a material 612 with pillars 611 that are fabricated completely through material 612 from one surface of the material in one direction. Through-material pillars may be preferable in some embodiments because they may provide uniform depth and conductivity because the through-material pillars perfectly match the thickness of the material they penetrate. As described further below, uniform depth and conductivity may improve fingerprint sensing through the anisotropic conductive material. Material fabricated with through-material pillars may be ground to reduce the material to a desired thickness. After fabricating the pillars, one or both of the surfaces of material with though-material pillars may be covered by a thin layer of a cover material to provide a surface to receive a fingerprint. The cover material would be of controlled thickness across the surface of the anisotropic conductive material. FIG. 6B illustrates a material 622 with pillars 621 that are fabricated completely through material 622, and with a cover material 623. FIG. 6C illustrates a material 632 with pillars 631 that are fabricated completely through material 632, and with a cover material 633.

FIG. 6B illustrates a material 622 with pillars 621 that are fabricated partly through material 622. Pillars fabricated partially through a material may be called "blind pillars." Blind pillars may eliminate the need to attach an intermediate material to provide a surface to receive a fingerprint. Material fabricated with blind pillars may be ground to reduce the material to a desired thickness.

Pillars may be fabricated in different shapes. FIGS. 6A-5C illustrate pillars 611, 621, and 631 formed in the shape of a cylinder. FIG. 7A illustrates a material 710 with pillars 711 formed in the shape of a cone. FIG. 7B illustrates a material 720 with pillars 721 formed in the shape of a cylinder with plates 722 at each end. A cylinder with one or two plates 722 may have smaller capacitive coupling to neighboring pillars than cylinders, while providing large areas at each surface for strong coupling to a fingerprint and a fingerprint sensor. In other embodiments, the pillars may be formed in other shapes.

Figure 8A:
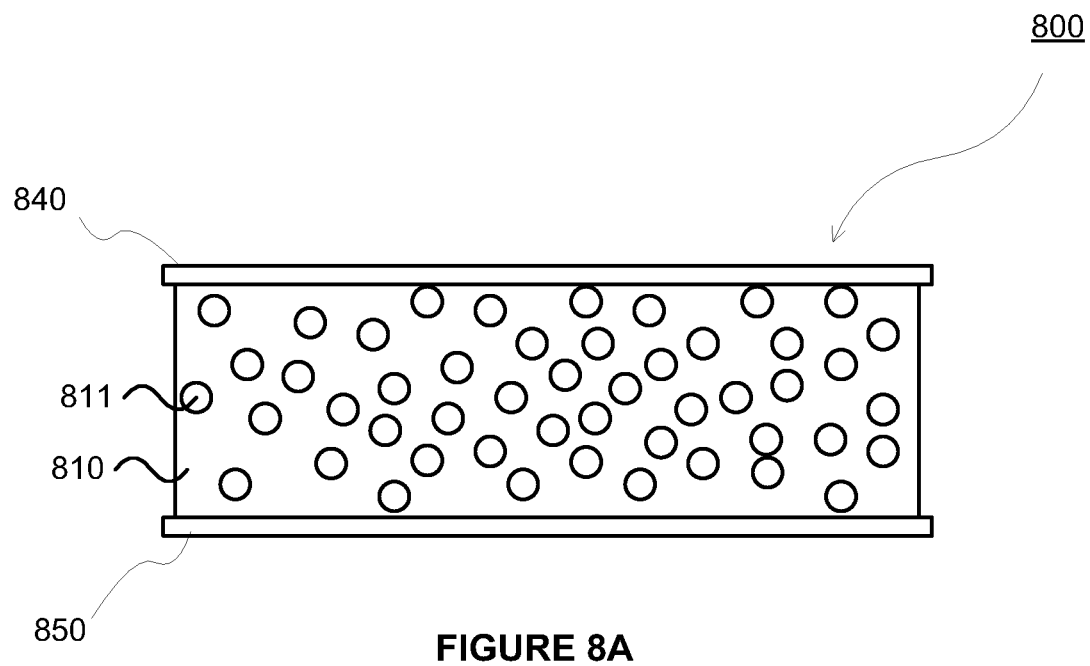
FIGS. 8A-8B illustrate a material in which conductive elements have been incorporated into the material according to various embodiments.
Figure 8B:
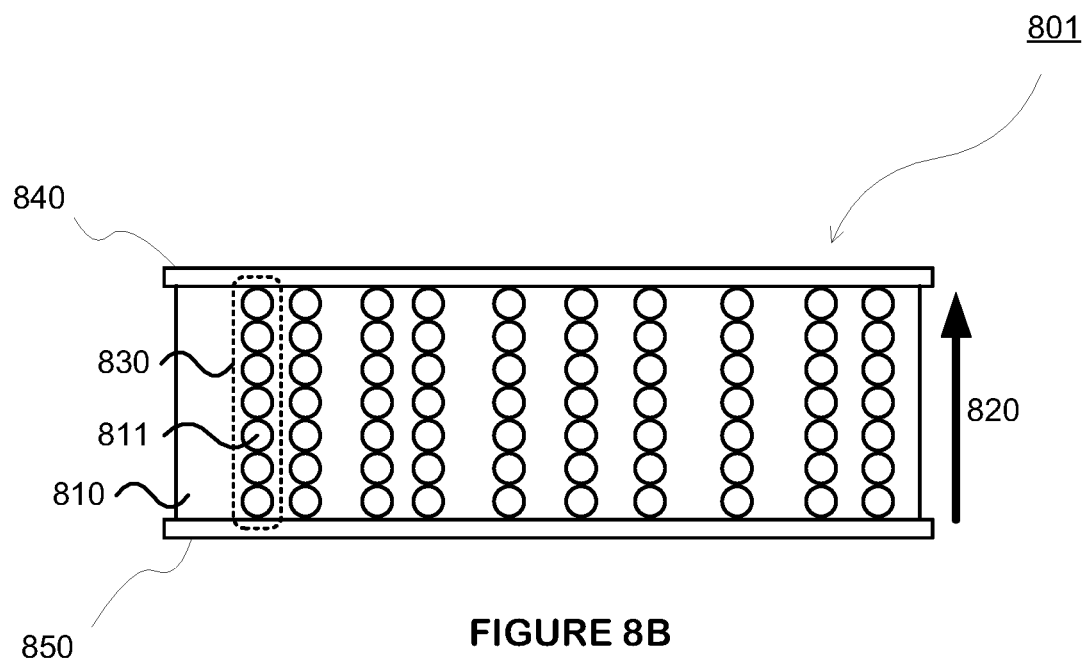

FIGS. 8A and 8B illustrate another method to fabricate anisotropic conductive material by incorporating conductive elements in a material. FIG. 8A illustrates a material 810 in which conductive elements 811 have been randomly incorporated. In an embodiment, the embedded conductive particles may be less than 20 μm in diameter. FIG. 8B illustrates material 810 after an electric or magnetic field force 820 has been applied across material 810 during a manufacturing step. Electric or magnetic field 820 may be applied in a direction substantially orthogonal to material surface 840 and material surface 850. The direction of applied electric or magnetic field 820 is indicated by the arrow. The electric or magnetic field force may align conductive elements 811 in the direction of the applied electric or magnetic field 820, thus forming the equivalent of "pillars" 830 aligned in the direction of the applied electric or magnetic field 820. Thus, material 810 will have increased conductivity in the alignment direction of pillars 830. In a specific embodiment, the conductive elements are ferro-electric conductive particles and a magnetic field has been applied. In other embodiments, other conductive elements 811 such as conductive filaments may be used. In other embodiments, conductive elements 811 may be aligned to form the equivalent of pillars 830 by applying an electric field across material 810 in a direction substantially orthogonal to material surface 840 and material surface 850. In still other embodiments, conductive elements 811 may be aligned to form the equivalent of pillars 830 by applying pressure across material 810 in a direction substantially orthogonal to material surface 840 and material surface 850.

Figure 9A:
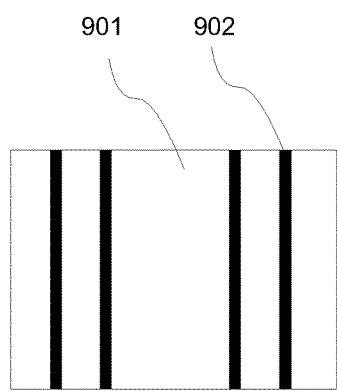
FIGS. 9A-9C illustrate a material in which conductive elements have been incorporated into the material according to various embodiments.
Figure 9B:
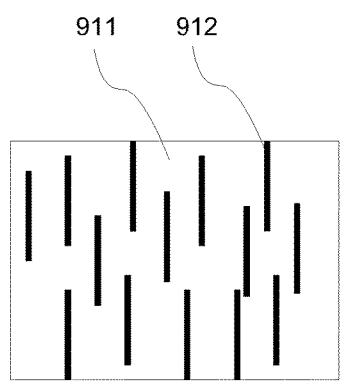
Figure 9C:
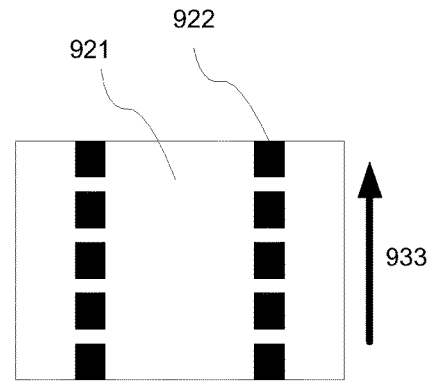

FIGS. 9A-9B illustrate another method to fabricate anisotropic conductive material by incorporating conductive elements in a material. FIG. 9A illustrates a material 901 in which conductive elements 902 have been fabricated in a material such that the conductive elements are aligned from one surface to a second surface of the material and reach through the material in one direction, forming "pillars." FIG. 9B illustrates a material 911 in which conductive elements 912 have been fabricated in a material such that the conductive elements are aligned from one surface of the material to a second surface of the material in one direction but do reach through the material, forming "pillars." FIG. 9C illustrates a material 921 in which conductive elements 922 have been fabricated in a material such that the conductive elements are aligned in direction 933 from one surface of the material, and where the distance between the conductive elements in direction 933 is smaller than the distance between the conductive elements in other directions, forming "pillars." Thus, material 901, 911, and 921 will have increased conductivity in the alignment direction 933 of the pillars. The conductive elements of FIGS. 9A-9C may comprise, but are not limited to, nano-wires, flakes, microparticles, or bars. The conductive elements illustrated in FIGS. 9A-9C may comprise conductive elements which are the same or similar to those disclosed in FIGS. 6A-6C, 7A-7B, and 8A-8B.

Anisotropic conductive material may be fabricated with rigid materials including, but not limited to, glass, ceramic, or plastic. Anisotropic conductive material may be fabricated with non-rigid materials including, but not limited to, film or fabric.

Anisotropic Conductive Material and Fingerprint Sensing

Figure 10A:
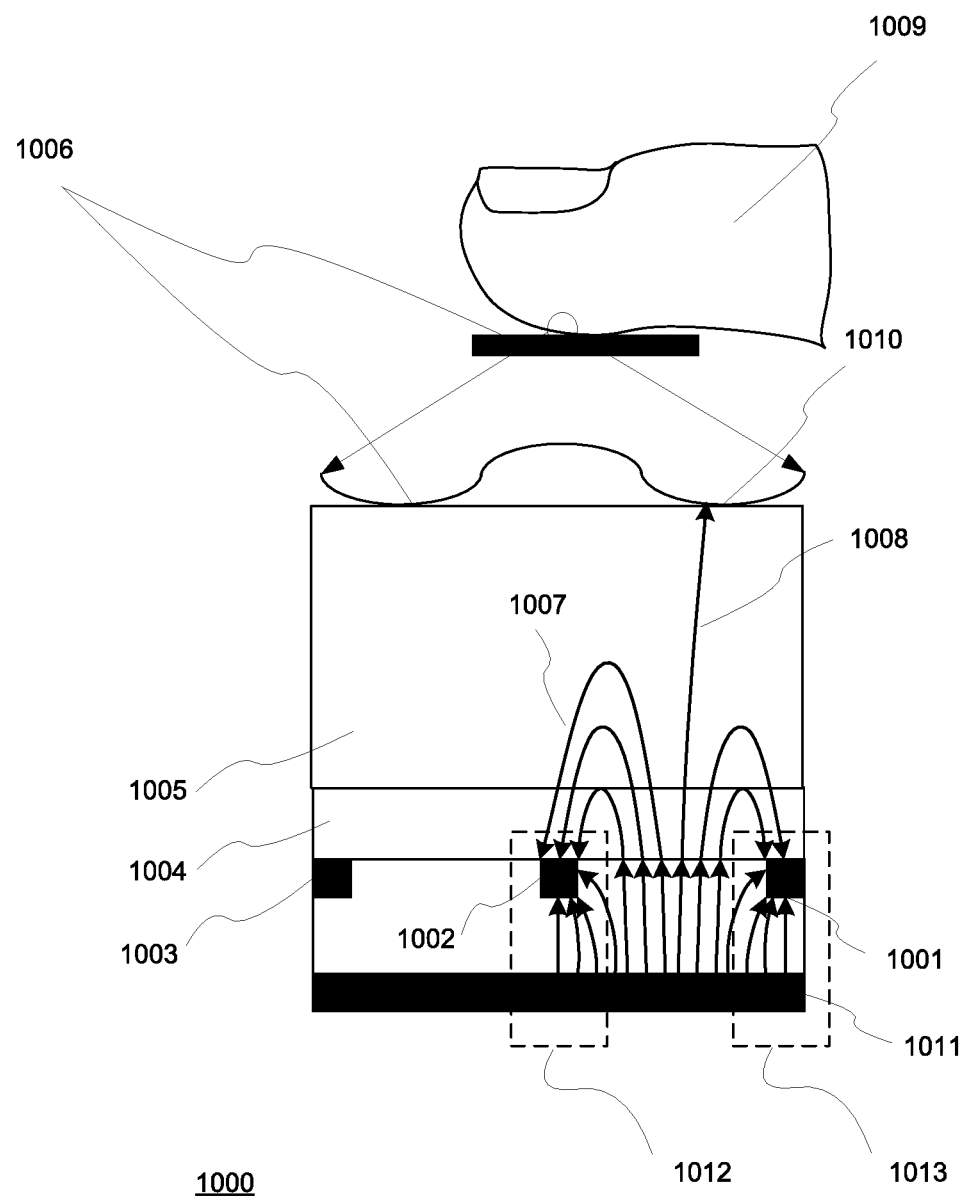
FIGS. 10A-10B illustrates the effect of anisotropic conductive material on the electric field density of a capacitive fingerprint sensor according to various embodiments.
Figure 10B:
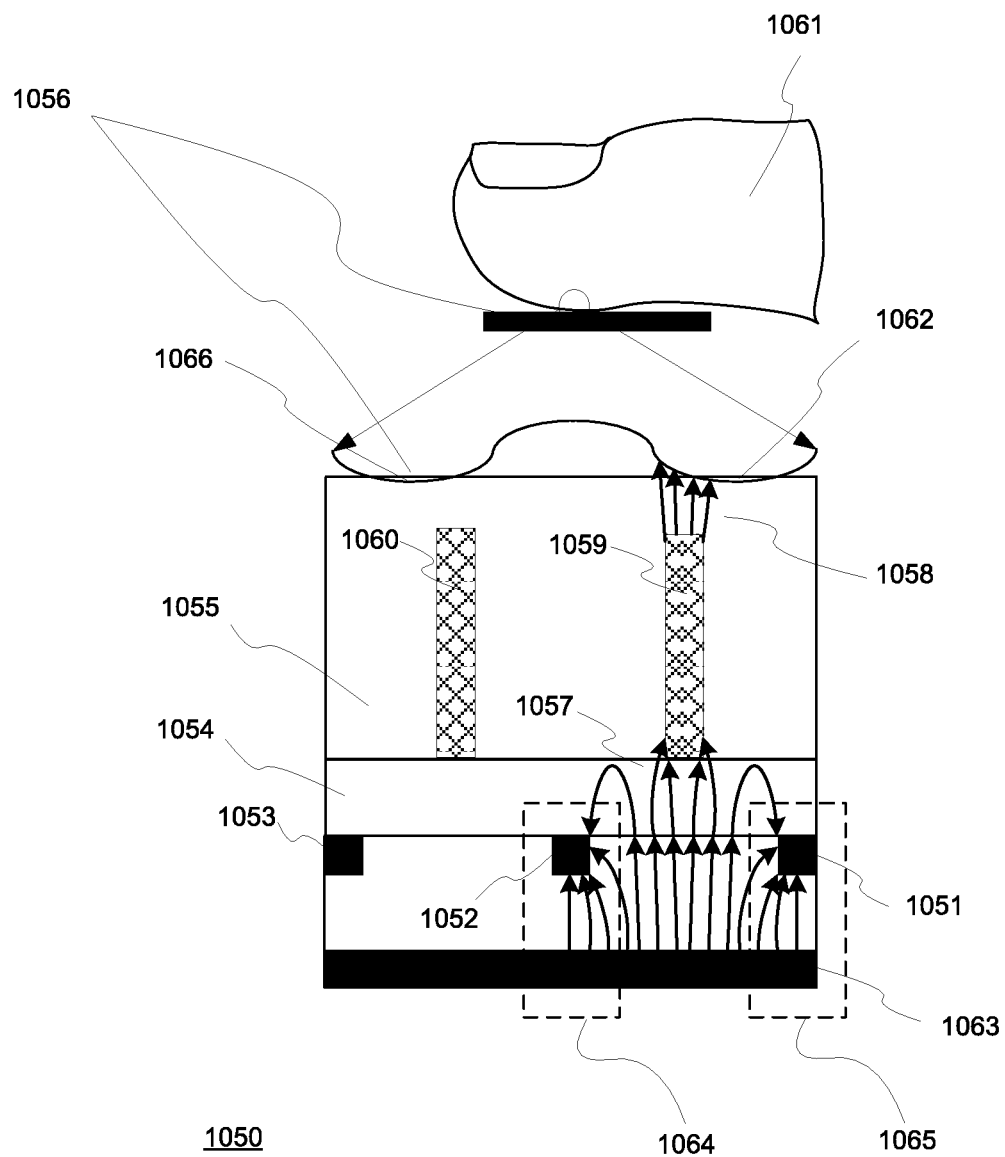

FIGS. 10A and 10B illustrate the effect of pillars in anisotropic conductive material on the electric field density of a capacitive fingerprint sensor which is imaging a fingerprint. FIG. 10A illustrates a mutual capacitance fingerprint sensor 1000 comprising Tx electrode 1011, Rx electrodes 1001, 1002, and 1003, sensor surface 1004, and overlay material 1005. In this example, a sense element comprises the intersection of Tx electrode 1011 and an Rx electrode 1001, 1002, or 1003. Sense element 1012 comprises the intersection of Tx electrode 1011 and Rx electrode 1002; sense element 1013 comprises the intersection of Tx electrode 1011 and Rx electrode 1001. In this example, Rx electrodes 1001, 1002, and 1003 correspond to column electrodes 404 in FIG. 4, and Tx electrode 1011 corresponds to column electrodes 406 in FIG. 4. Mutual capacitance fingerprint sensor 1000 measures the change in mutual capacitance of sense elements 1012 or 1013 in the presence of finger 1009 on a surface 1006 of overlay material 1005. The magnitude of the decrease in mutual capacitance measured by sense elements 1012 and 1013 is represented by the number of field lines 1007 which couple from Tx electrode 1011 to finger 1009 instead of coupling to Rx electrodes 1001 and 1002. In this example, the field lines are an abstraction of the strength of capacitive coupling between sense elements 1012 and 1013 and finger 1009. FIG. 10A illustrates that fingerprint ridge 1010 is weakly coupled to sense elements 1012 and 1013 through material 1005, causing a slight decrease in measured mutual capacitance, as represented by the single field line 1008 that is shunted away from sense elements 1012 and 1013 to ridge 1010.

FIG. 10B illustrates a mutual capacitance fingerprint sensor 1050 comprising Tx electrode 1063, Rx electrodes 1051, 1052, and 1053, sensor surface 1054, and overlay material 1055. In this example, a sense element comprises the intersection of Tx electrode 1063 and an Rx electrode 1051, 1052, or 1053. Sense element 1064 comprises the intersection of Tx electrode 1063 and Rx electrode 1052; sense element 1064 comprises the intersection of Tx electrode 1011 and Rx electrode 1051. Overlay material 1055 comprises pillars 1059 and 1060. The magnitude of the decrease in mutual capacitance measure by sense elements 1064 and 1065 in the presence of finger 1061 on a surface 1056 of the overlay material is represented by the number of field lines 1058 which couple from Tx electrode 1063 to finger 1061 instead of coupling to Rx electrodes 1064 and 1065. FIG. 10B illustrates that fingerprint ridge 1062 is strongly coupled to sense elements 1064 and 1065 through pillar 1059, causing a decrease in measured mutual capacitance, as represented by the four field lines 1058 that are coupled away from sense elements 1064 and 1065 to ridge 1062 through pillar 1059. In other words, pillar 1059 acts as an electric field guide that increases the capacitive coupling of fingerprint ridge 1062 to the sense elements 1064 and 1065, and increases the change in measured capacitance of sense elements 1064 and 1065. The increase in the magnitude of the decrease in measured mutual capacitance using material 1055 comprising pillars 1059 and 1060 compared to material 1005 without pillars is represented by the increase in the number of field lines 1057 that are coupled away from sense elements 1064 and 1065 to fingerprint ridge 1062. In the examples of FIGS. 10A and 10B, the increase using material 1055 with pillars 1059 and 1060 is represented by the four field lines 1058 compared to the one field line 1008 for material 1005 without pillars. It is to be understood that conductively anisotropic material may similarly be used with self-capacitance fingerprint sensors where the increased capacitive coupling of the pillar causes an increase in the measured change in capacitance by sense elements. It is also to be understood that the alignment of pillars 1059 and 1060 to fingerprint ridges 1062 and 1066 is exemplary only; pillars may or may not be aligned with fingerprint ridges and/or fingerprint valleys.

Figure 11A:
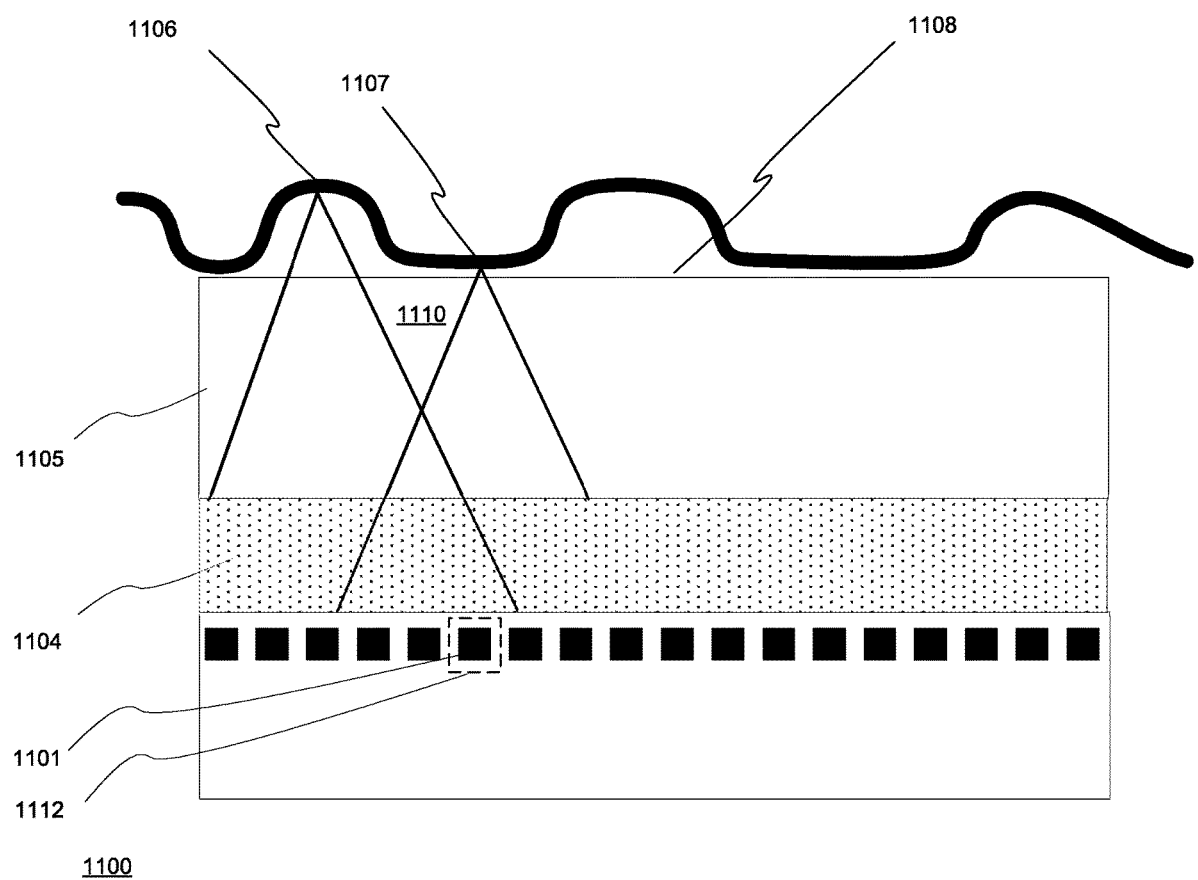
FIGS. 11A-11B illustrate the effect of anisotropic conductive material on the imaging of a fingerprint by a fingerprint sensor according to various embodiments.
Figure 11B:
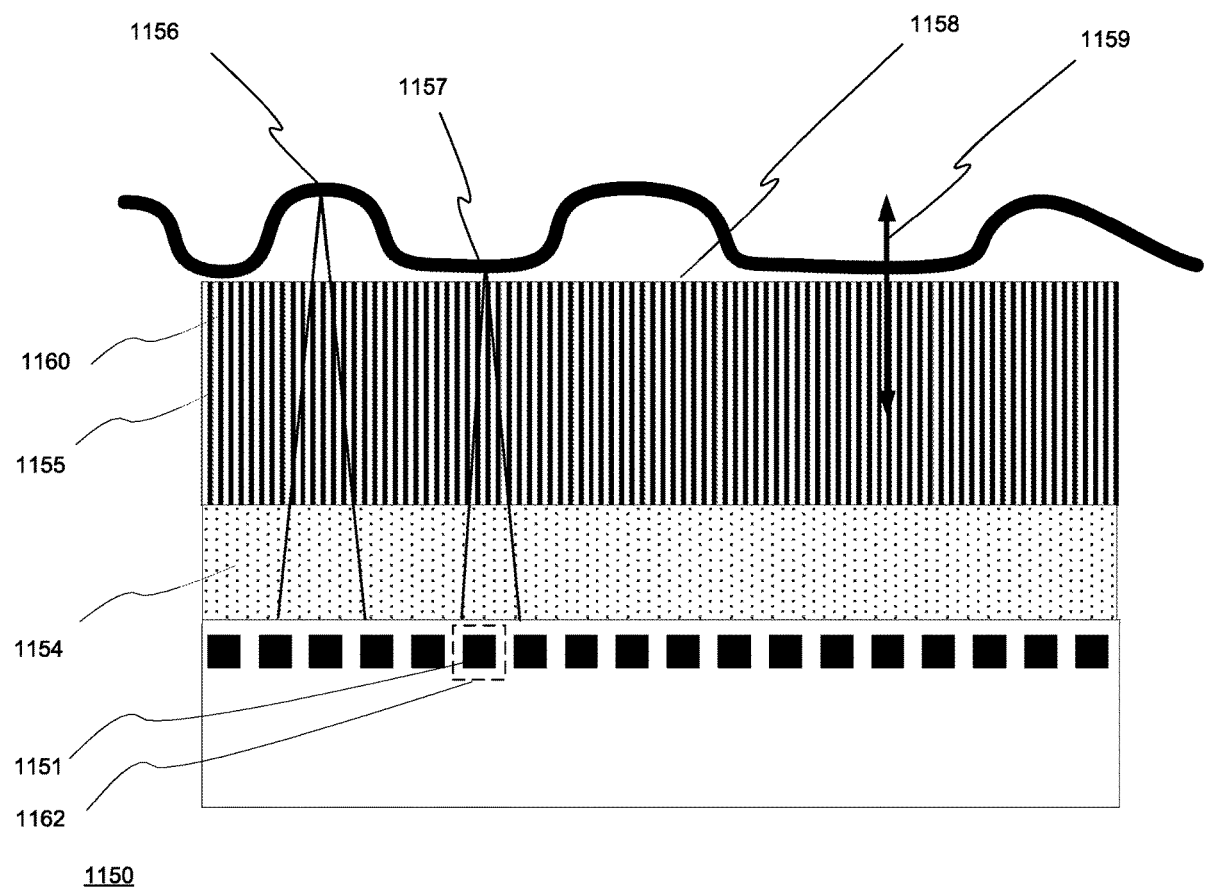

FIGS. 11A and 11B illustrate another example of the effect of anisotropic conductive material on the imaging of a fingerprint by a fingerprint sensor. FIG. 11A illustrates a self capacitance fingerprint sensor 1100 comprising electrode 1101, sensor surface 1104, and overlay material 1105. In this example, sense element 1112 comprises electrode 1101. Self capacitance fingerprint sensor 1100 measures the change in self capacitance of sense element 1112 in the presence of fingerprint feature 1106, corresponding to a fingerprint valley, and fingerprint feature 1107, corresponding to a fingerprint ridge, on surface 1108 of overlay material 1105. Fingerprint features 1106 and 1107 disperse as they capacitively couple through overlay material 1105 to sense element 1112. The dispersion, or "blurring", of fingerprint features 1106 and 1107 through overlay material 1105 is represented by lines 1110. In this example, lines 1110 are an abstraction of the dispersion of fingerprint features 1106 and 1107 through overlay material 1105 to sense elements 1112. FIG. 11A illustrates that dispersion of fingerprint features 1106 and 1107 through overlay material 1105 may enable each fingerprint feature 1106 and 1107 to capacitively couple to multiple sense elements 1112, and also may enable sense element 1112 to capacitively couple to multiple fingerprint features 1106 and 1107. Increasing the number of fingerprint features 1106 and 1107 that capacitively couple to a sense element 1112, or increasing the number of sense elements 1112 that capacitively couple to each of fingerprint features 1106 and 1107, reduces the accuracy of fingerprint imaging by sense element 1112 and, therefore, by fingerprint sensor 1100.

FIG. 11B illustrates a self capacitance fingerprint sensor 1150 comprising electrode 1151, sensor surface 1154, and anisotropic conductive material 1155. The direction of increased conductivity in anisotropic conductive material 1155 is represented by arrow 1159. In this example, sense element 1162 comprises electrode 1151. Self capacitance fingerprint sensor 1150 measures the change in self capacitance of sense element 1162 in the presence of fingerprint features 1156 and 1157 on surface 1158 of anisotropic conductive material 1155. Fingerprint features 1156 and 1157 may disperse as they capacitively couple through anisotropic conductive material 1155 to sense element 1162. The dispersion of fingerprint features 1156 and 1157 through anisotropic conductive material 1155 is represented by lines 1160. FIG. 11B illustrates that dispersion of fingerprint features 1156 and 1157 through anisotropic conductive material 1155 is less than dispersion of dispersion of fingerprint features 1106 and 1107 through overlay material 1105 as illustrated in FIG. 11A. The pillars (not shown) of anisotropic conductive material 1155 may act like electric field guides that decrease the dispersion of the fingerprint features as sensed by sense element 1162. Reducing the dispersion of fingerprint features 1156 and 1157 may enable each fingerprint feature 1156 and 1157 to capacitively couple to fewer sense elements 1162, and may enable each sense element 1162 to capacitively couple to fewer fingerprint features 1156 and 1157, thus increasing the accuracy of fingerprint imaging by fingerprint sensor 1150. It is to be understood that conductively anisotropic material may similarly be used with mutual capacitance fingerprint sensors where the reduced dispersion of fingerprint features may also enable each fingerprint feature to capacitively couple to fewer sense elements 1162, and may enable each sense element to capacitively couple to fewer fingerprint features, thus increasing the accuracy of fingerprint imaging by the mutual fingerprint sensor.

Figure 12A:
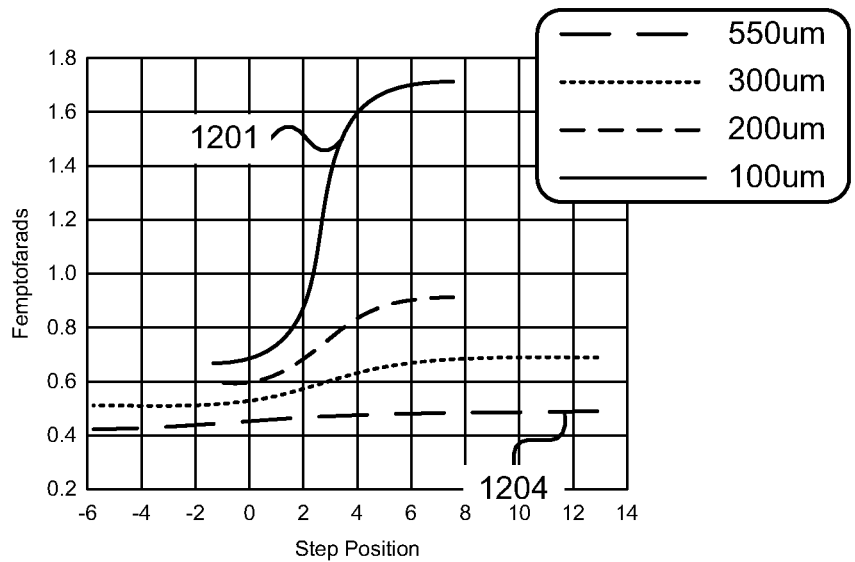
FIGS. 12A-12B illustrate measured capacitance according to various embodiments.
Figure 12B:
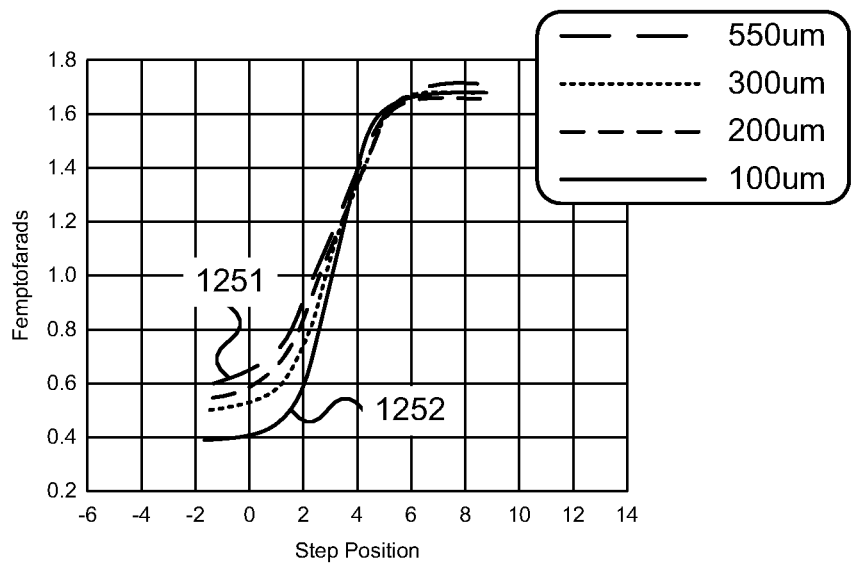

FIGS. 12A and 12B further illustrate an example of the effect of anisotropic conductive material on the imaging of a finger by a fingerprint sensor using self-capacitance. In the graphs of FIGS. 12A and 12B, the y-axes represent the measured capacitance in femtofarads (fF). Position 0 on the x-axes represents a transition between a valley of an imaged fingerprint and a ridge. The graphs illustrate the change in measured capacitance between a fingerprint valley and a fingerprint ridge using overlay materials of varying thickness (100 μm-550 μm) which are in contact with both the fingerprint and the fingerprint sensor surface. FIG. 12A illustrates the change in measured capacitance using overly material without pillars. Line 1201 indicates the measured capacitance of an imaged fingerprint where the overlay material is 110 μm thick. At x-axis position −2, corresponding to a valley, the measured capacitance on line 1201 is approximately 0.6 fF. At x-axis position 7, corresponding to a ridge, the measured capacitance of line 1201 is approximately 1.7 fF. Thus, the measured change in capacitance of line 1201 is approximately 1.1 fF. Line 1204 indicates the measured capacitance of an imaged fingerprint where the overlay material is 650 μm. At x-axis position −2, corresponding to a valley, the measured capacitance of line 1204 is approximately 0.35 fF. At x-axis position 7, corresponding to a ridge, the measured capacitance of line 1204 is approximately 0.40 fF. Thus, the measured change in capacitance of line 1204 is approximately 0.05 fF.

FIG. 12B illustrates an example of the change in measured capacitance using overlay material with pillars. Line 1251 indicates the measured capacitance of an imaged fingerprint where the overlay material with pillars is 110 μm. At x-axis position −2, corresponding to a valley, the measured capacitance of line 1251 is approximately 0.4 fF. At x-axis position 7, corresponding to a ridge, the measured capacitance of line 1251 is approximately 1.7 fF. Thus, the measured change in capacitance of line 1251 is approximately 1.3 fF. Line 1254 indicates the measured capacitance of an imaged fingerprint where the overlay material with pillars is 650 μm. At x-axis position −2, corresponding to a valley, the measured capacitance of line 1254 is approximately 0.6 fF. At x-axis position 7, corresponding to a ridge, the measured capacitance of line 1214 is approximately 1.7 fF. Thus, the measured change in capacitance is approximately 1.1 fF.

As shown in FIGS. 12A and 12B, the measured change in capacitance using conventional material (without pillars) decreases significantly as the overlay thickness increases. The measured change in capacitance does not decrease as much using material with pillars as the overlay thickness increases. In other words, the pillars act like an electric field guide that increases the capacitive coupling of fingerprint features to the sense elements, reducing the decrease in the measured change in capacitance due to proximity of fingerprint features such as ridges through a thick overlay. The use of an overlay with pillars thus substantially increases the thickness of the overlay material through which the fingerprint sensor may accurately image a fingerprint.

The accuracy of fingerprint imaging increases as the number of capacitive sense elements that may detect each fingerprint features increases. Increasing the density of pillars relative to capacitive sense elements increases the number of sense elements that may couple to each fingerprint feature strongly enough to detect the fingerprint feature. Increasing the density of pillars relative to capacitive sense elements also decreases the effect of the alignment of pillars to sense elements. Thus, increasing the density of pillars increases the accuracy of fingerprint imaging through an overlay. Increasing the density of pillars also increases the thickness of an overlay that may enable accurate imaging of a fingerprint.

Decreasing the density of pillars relative to capacitive sense elements increases the effect of the alignment of pillars to sense elements. In an embodiment where there is one pillar for each capacitance sense element, alignment of each pillar to a sense element increases the coupling of fingerprint features to each sense element, thus increasing the accuracy of fingerprint imaging. In a specific embodiment where there is one pillar for each capacitance sense element, centering the pillars in each unit cell provides the most effective conductive coupling and the most accurate fingerprint imaging.

In an embodiment where there is less than one pillar for each capacitance sense element, accuracy of fingerprint imaging through an overlay is less than embodiments with one or more pillars for each capacitance sense element. However, accuracy of fingerprint imaging through an overlay with less than one pillar for each capacitance sense element is greater than accuracy of fingerprint imaging through an overlay without pillars.

In an embodiment, the pillars may be in direct physical contact with the sense elements. In other embodiments, for ease of fabrication, the pillars may not be in direct physical contact with the sense elements. In an embodiment where pillars are in direct physical contact with to the sense elements, accuracy of fingerprint imaging through an overlay is greater than embodiments where pillars are not in direct physical contact with the sense elements. However, accuracy of fingerprint imaging through an overlay where pillars are not in direct physical contact with the sense elements is greater than accuracy of fingerprint imaging through an overlay without pillars.

FIGS. 13A-D illustrate embodiments where pillars are arranged symmetrically around an axis in the direction of the pillars with a uniform density of one pillar per mutual capacitance sense element. FIGS. 13A-D illustrate four symmetric arrangements of pillars 1301 with a uniform density of one pillar per mutual capacitance sense element 1303, sense element 1303 comprising the intersection of Rx electrode 1302 and Tx electrode 1304.

FIGS. 13E-F illustrate embodiments where pillars are arranged symmetrically around an axis in the direction of the pillars with a uniform density of two pillars per mutual capacitance sense element. FIGS. 13E-F illustrate two symmetric arrangements of pillars with a uniform density of two pillars 1301 per mutual capacitance sense element 1303, sense element 1303 comprising the intersection of Rx electrode 1302 and Tx electrode 1304.

Figure 13A:
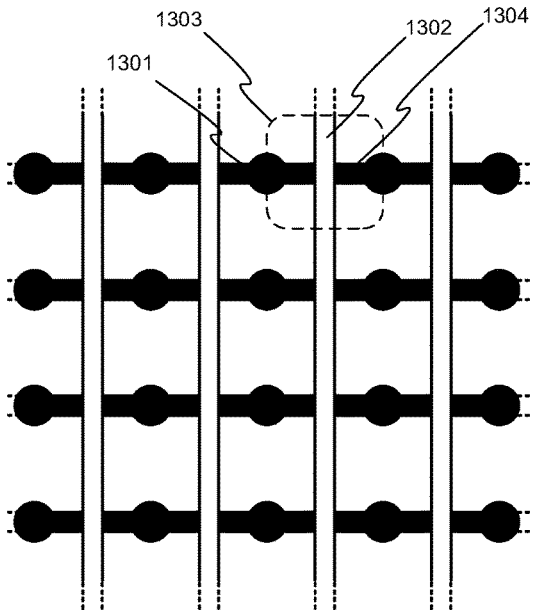
Figure 13B:
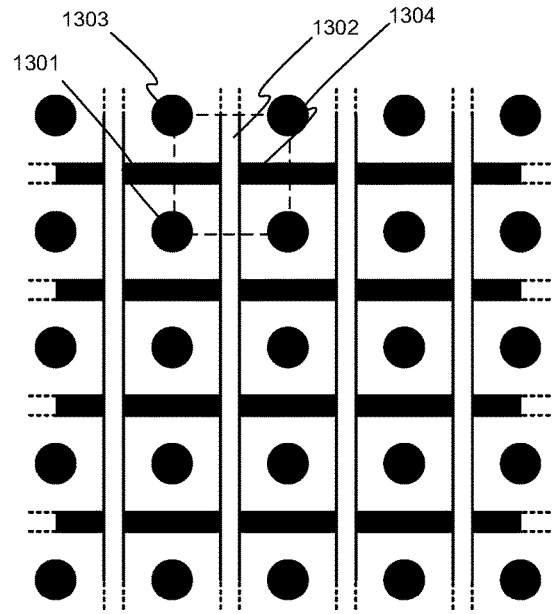
Figure 13C:
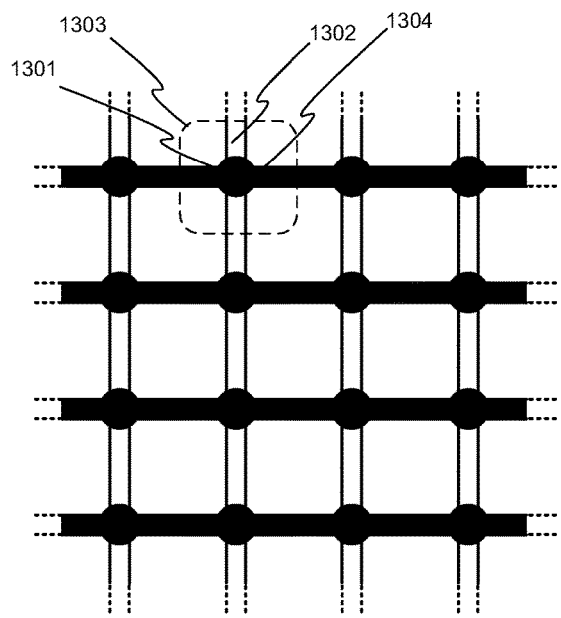
Figure 13D:
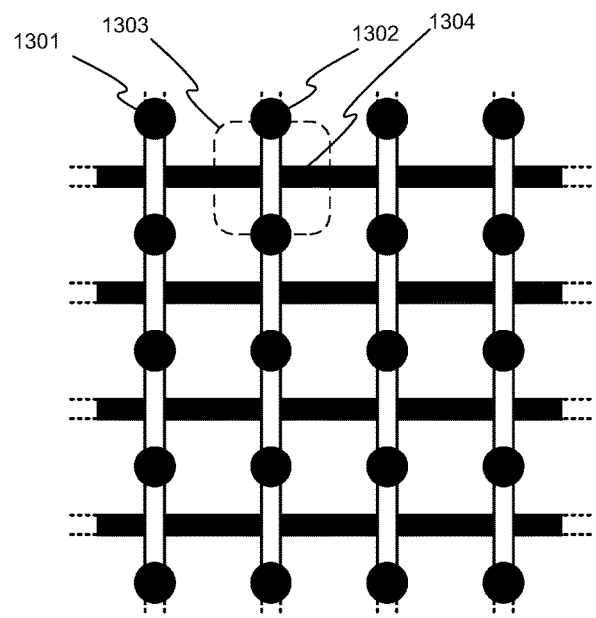
Figure 13G:
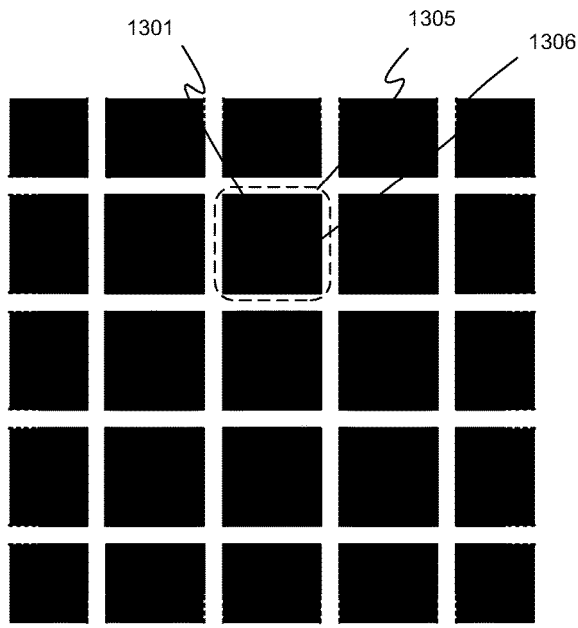
Figure 13H:
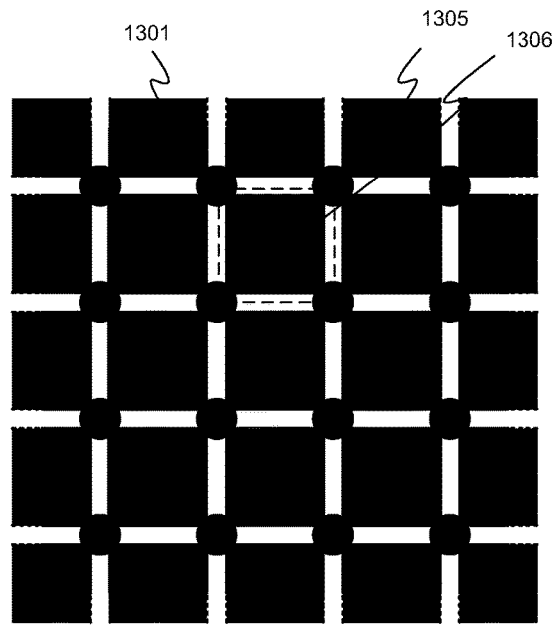

FIGS. 13G-H illustrate embodiments where pillars are arranged symmetrically around an axis in the direction of the pillars with a uniform density of one pillar per self capacitance sense element. FIGS. 13G-H illustrate two symmetric arrangements of pillars 1301 with a uniform density of one pillar per self capacitance sense element 1305, sense element 1305 comprising electrode 1306.

Figure 13I:
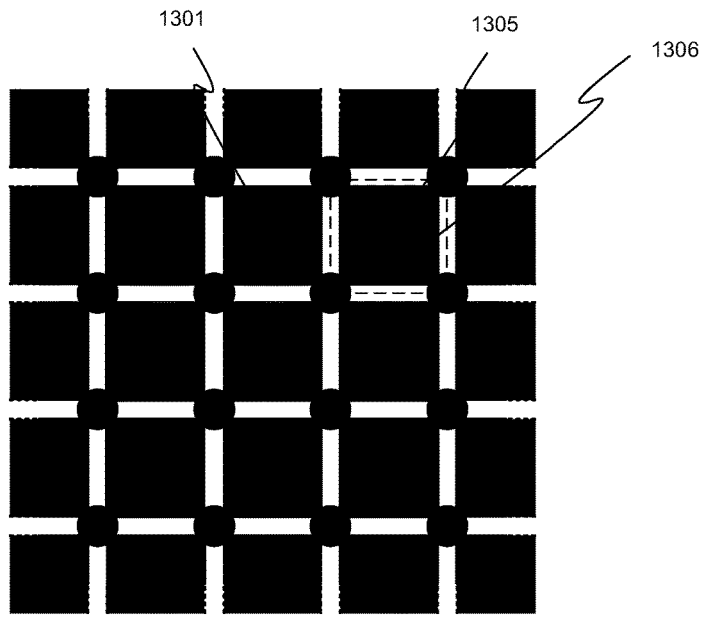

FIG. 13I illustrates an embodiment where pillars are arranged symmetrically around an axis in the direction of the pillars with a uniform density of two pillars per self capacitance sense element. FIG. 13I illustrates a symmetric arrangement of pillars 1301 with a uniform density of two pillars per self capacitance sense element 1305, sense element 1305 comprising electrode 1306.

It is to be understood that anisotropic material may comprise pillars with a relative density of more than two pillars per capacitive sense element for both mutual capacitance and self capacitance.

Figure 14:
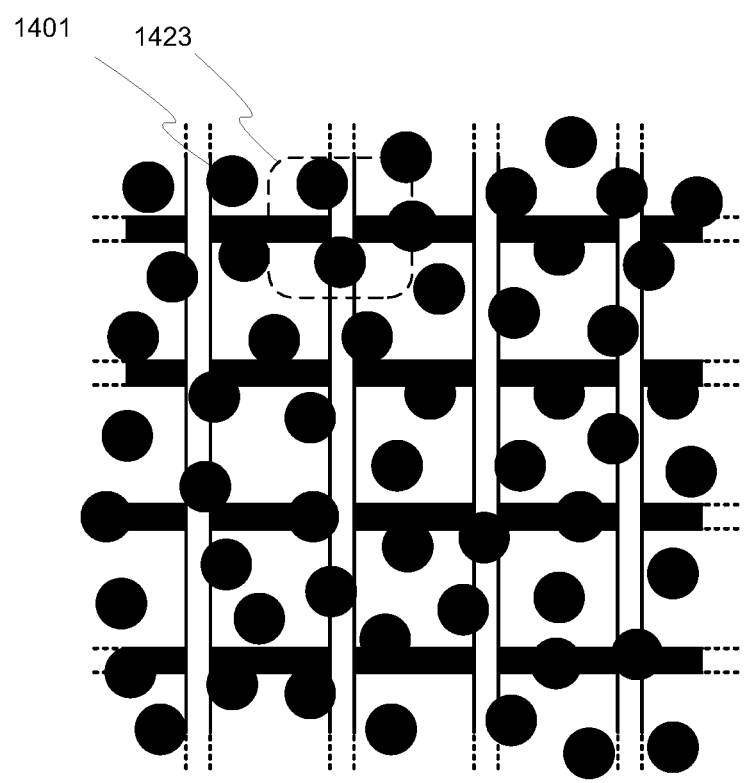
FIG. 14 illustrates an arrangement of pillars according to an embodiment.

FIG. 14 illustrate an embodiment where pillars 1401 are arranged randomly and asymmetrically around an axis in the direction of the pillars with a uniform density of one pillar per mutual capacitance sense element 1402. An asymmetric arrangement of pillars may be desirable for ease of fabrication. A random arrangement of pillars may also be desirable for ease of fabrication. An asymmetric arrangement of pillars may be desirable in flexible material, to allow the material to flex yet still provide effective conductive coupling through the pillars. When the pillars have an asymmetric arrangement, the fingerprint sensor may more accurately image a fingerprint when the asymmetric pillars have a uniform distribution density. When the pillars have an asymmetric arrangement, increasing the density of pillars relative to capacitive sense elements increases the number of sense elements that may couple to each fingerprint feature strongly enough to detect the fingerprint feature. Thus, increasing the density of asymmetrically arranged pillars increases the accuracy of fingerprint imaging.

It is to be understood that a self capacitance fingerprint sensor may also more accurately image a fingerprint when asymmetric pillars have a uniform distribution density per self capacitance sense element, and that increasing the density of asymmetrically arranged pillars increases the accuracy of fingerprint imaging using self capacitance sense elements.

Figure 15:
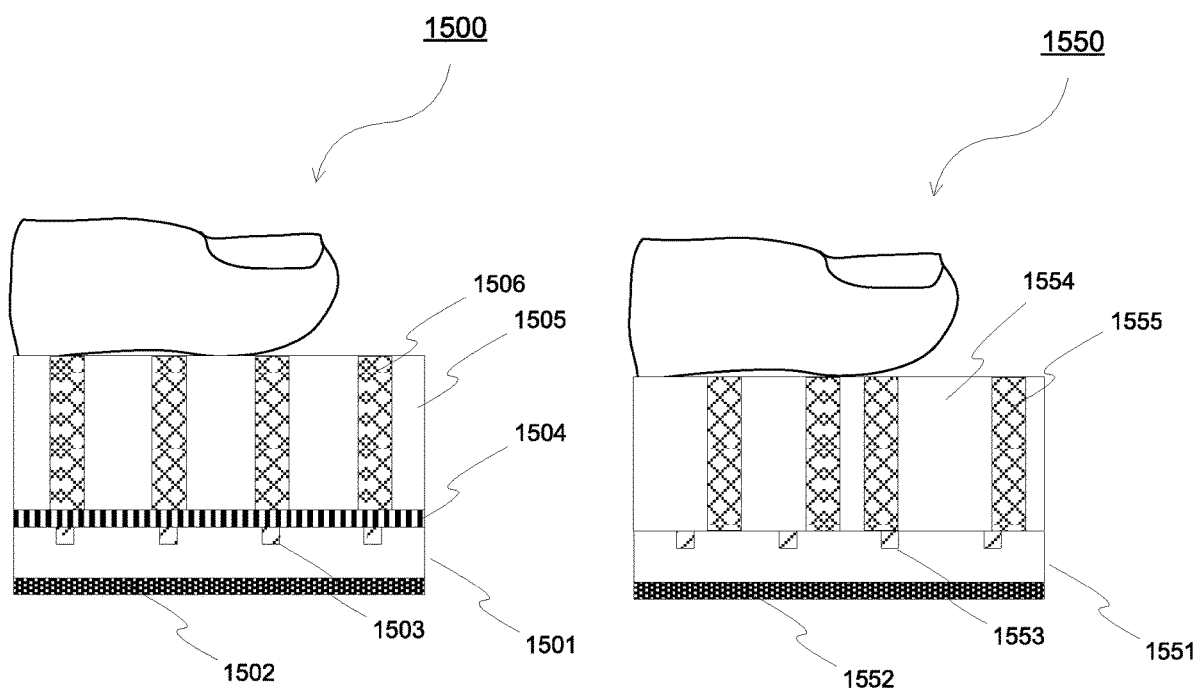
FIG. 15A-15B illustrate a fingerprint sensor structure according to various embodiments.

FIG. 15A illustrates a fingerprint sensor structure 1500 comprising a mutual capacitance fingerprint sensor 1501 with Tx electrodes 1502 and Rx electrodes 1503, intermediate material 1504, and overlay 1505. Intermediate material 1504 may be an adhesive or color-matching paint. Overlay 1505 comprises pillars 1506. In this embodiment, pillars 1506 are symmetrically arranged around an axis in the direction of the pillars, with a density of one pillar per mutual capacitance sense elements and pillars 1506 are aligned to the sense elements. It is to be understood that overlay 1505 may be fabricated with pillars 1506 in other arrangements. In the embodiment comprising an intermediate material 1504, it is to be understood that the intermediate material must allow adequate coupling between the fingerprint and the sense elements through the intermediate material and the overlay. In a specific embodiment, intermediate material 1504 may also comprise pillars; in various embodiments, overlay 1505 and intermediate material 1504 may be fabricated with the same or different arrangements of pillars.

FIG. 15B illustrates a fingerprint sensor structure 1550 comprising a mutual capacitance fingerprint sensor 1551 with Tx electrodes 1552 and Rx electrodes 1553. Overlay 1554 comprises pillars 1555. In this embodiment, the pillars are randomly and asymmetrically arranged around an axis in the direction of the pillars, with a density of one pillar per mutual capacitance sense elements and the pillars 1555 are not aligned to the sense elements, Rx electrodes 1553. This embodiment does not include an intermediate material.

Referring back to FIG. 6B, a fingerprint sensor structure may comprise an overlay comprising material 622, pillars 621, and cover layer 623. In the embodiment comprising an cover layer 623, it is to be understood that the cover layer 623 must allow adequate coupling between the fingerprint and the sense elements through cover layer 623 and material 622. In a specific embodiment, cover layer 623 may also comprise pillars; in various embodiments, material 622 and cover layer 623 may be fabricated with the same or different arrangements of pillars.

A fingerprint sensor overlay comprising anisotropic conductive material as described in reference to FIGS. 13A-14B may be fabricated with rigid materials including, but not limited to, glass, ceramic, or plastic, or may be fabricated with flexible materials including, but not limited to, film or fabric. A fingerprint sensor overlay comprising anisotropic conductive material as described above may be fabricated such that a surface may be able to conform to the curvature of a finger; in a specific embodiment the surface is not deformed by the fingerprint ridge/valley structure. A fingerprint sensor overlay comprising anisotropic conductive material that is flexible and/or has a surface that is conformable may be desirable for ease of fabrication or ease of use.

Figure 16:
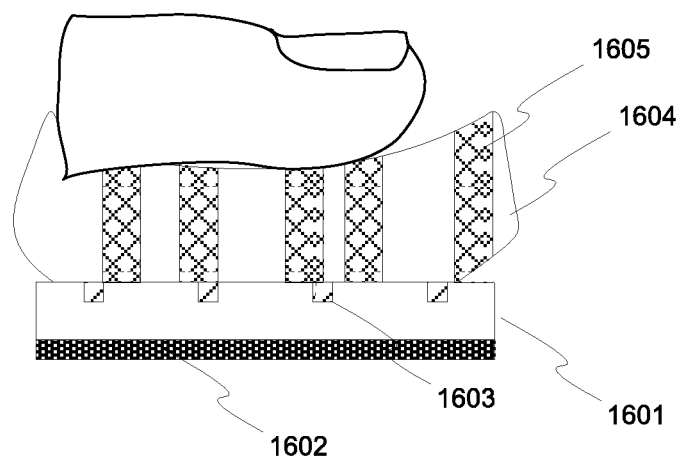
FIG. 16 illustrates a system fingerprint sensor structure according to an embodiment.

FIG. 16 illustrates a fingerprint structure 1600 comprising a mutual capacitance fingerprint sensor 1601 with Tx electrodes 1602 and Rx electrodes 1603. In this embodiment, overlay 1604 comprises flexible material with pillars 1605 arranged randomly and asymmetrically around an axis in the direction of the pillars with a density of one pillar per mutual capacitance sense elements. In another embodiment, the overlay may comprise a layer which is rigid and a cover layer which is flexible and/or has a surface which may be conformable.

Enclosure and Overlay Embodiments

Figure 17A:
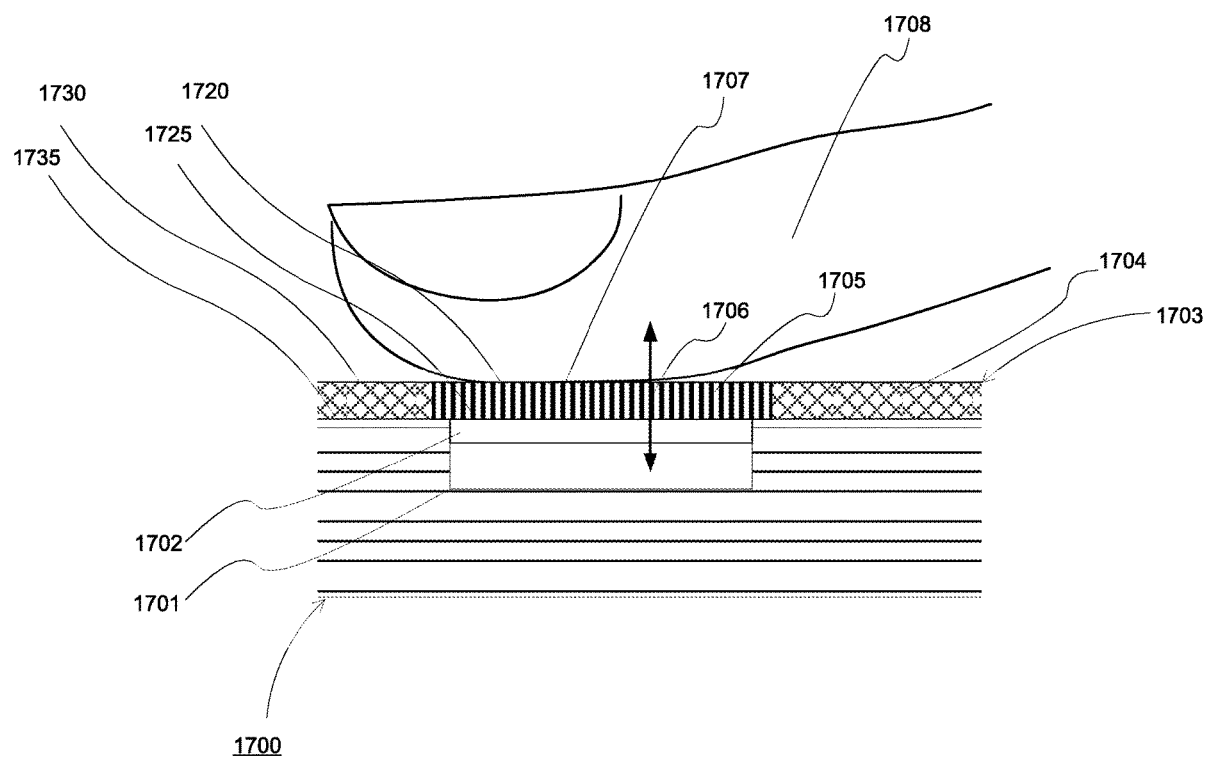
FIG. 17A-17C illustrates a system comprising an overlay, a fingerprint, and a fingerprint sensor according to various embodiments.

FIG. 17A illustrates an embodiment of an overlay comprising anisotropic conductive material disposed between a fingerprint and a fingerprint sensor. Device 1700 comprises fingerprint sensor 1701. Fingerprint sensor 1701 comprises sensor surface 1702. Overlay 1703 comprises intervening material 1704, which is configured to make contact with both fingerprint sensor surface 1702 and finger 1708. Anisotropic conductive material 1705 may be fabricated or inserted in the area of intervening material 1704 which is configured to contact both fingerprint sensor surface 1702 and finger pad 1707. In an embodiment, anisotropic conductive material 1705 may be fabricated or inserted in intervening material 1704 such that surface 1720 of anisotropic conductive material 1705 may be substantially level with surface 1730 of intervening material 1704, and such that surface 1725 of anisotropic conductive material 1705 is substantially level with surface 1735 of intervening material 1704. The direction of increased conductivity of anisotropic conductive material 1705 may be substantially orthogonal to surface 1720 and 1725 and is indicated by arrow 1706. Overlay 1703 may comprise rigid material such as glass, plastic, or ceramic. Overlay 1703 may comprise flexible material such as film or fabric. In an embodiment, some portions of overlay 1703 may be rigid while some portions may be flexible. Overlay 1703 may protect the device 1700 from harmful environmental factors, such as cold or water, and harmful physical factors, such as impacts, projectile objects, and corrosive chemicals.

Figure 17B:
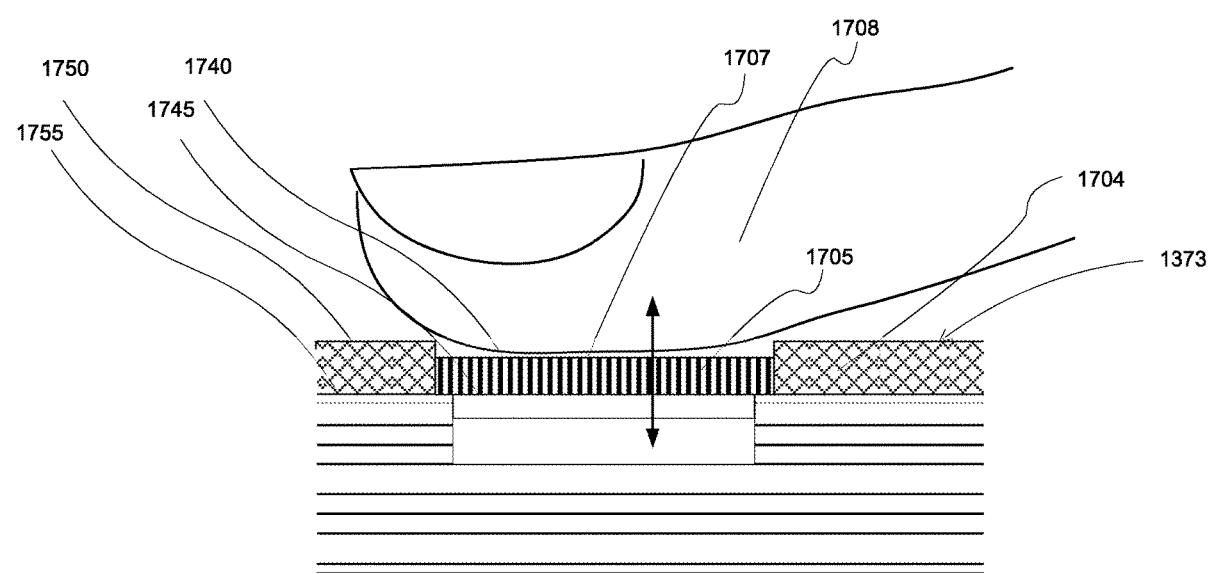

FIG. 17B illustrates an embodiment of overlay 1703 where anisotropic conductive material 1705 may be fabricated or inserted in intervening material 1704 such that surface 1745 of anisotropic conductive material 1705 is substantially level with surface 1755 of intervening material 1704, and such that surface 1740 of anisotropic conductive material 1705 is at a different level than surface 1750 of intervening material 1704. In the embodiment of FIG. 17B, surface 1750 of intervening material 1704 may be higher than surface 1740 of anisotropic conductive material 1705. In another embodiment, surface 1750 of intervening material 1704 may be lower than surface 1740 of anisotropic conductive material 1705. In other embodiments, surface 1740 of anisotropic conductive material 1705 may be partially covered by surface 1750 of intervening material 1704. Different surface levels of intervening material 1704 and anisotropic conductive material 1705 may provide tactile feedback, or a "guide," for placement of finger pad 1707 of finger 1708.

Figure 17C:
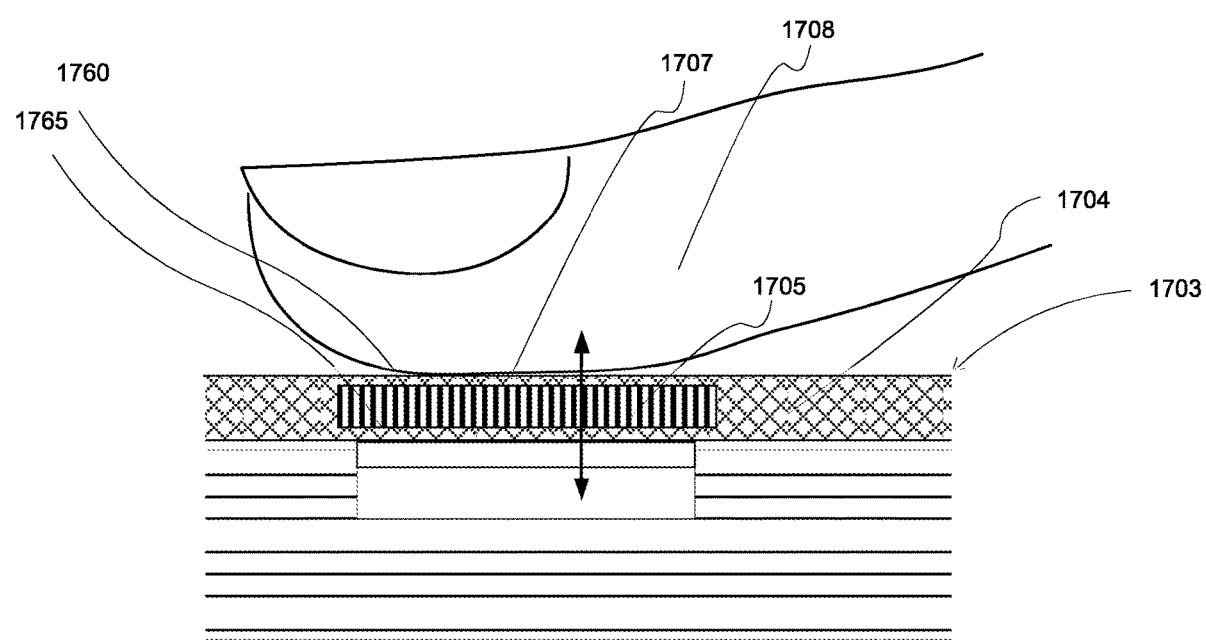

FIG. 17C illustrates an embodiment of overlay 1703 where anisotropic conductive material 1705 may be fabricated or inserted in intervening material 1704 such that anisotropic conductive material 1705 may be surrounded by intervening material 1704. In the embodiment of FIG. 17C, anisotropic conductive material 1705 may completely surrounded by intervening material 1704. In another embodiment, surface 1760 of anisotropic conductive material 1705 may be completely covered by of intervening material 1704, and surface 1765 of anisotropic conductive material 1705 may not be covered by intervening material 1704 (as illustrated by surface 1725 in FIG. 17A and surface 1745 in FIG. 17B). In another embodiment, surface 1765 of anisotropic material 1705 may be completely covered by of intervening material 1704, and surface 1760 of anisotropic material 1705 may not be covered by intervening material 1704 (as illustrated by surface 1720 in FIG. 17A and surface 1740 in FIG. 17B).

As illustrated in FIGS. 2 and 3, device 1700 may include a fingerprint controller (not shown), which may be configured to convert measured capacitance of fingerprint sensor 1701 into fingerprint data. Device 1700 may comprise a processor (not shown) which may further process fingerprint data or store fingerprint data in a memory. Device 1700 may comprise a memory (not shown) to store fingerprint data. In other embodiments, device 1700 may be configured to communicate with a controller, processor, or memory located in another device.

Figure 18:
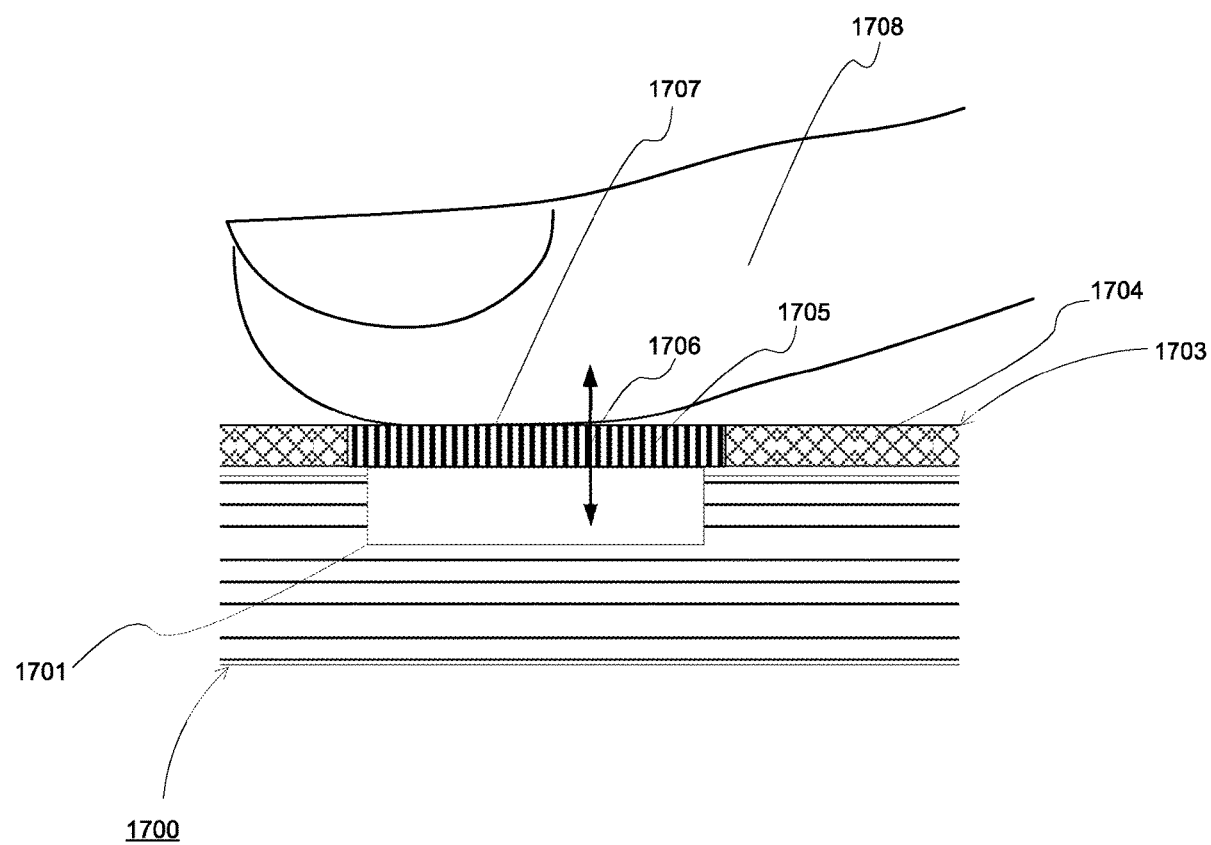
FIG. 18 illustrates a system comprising an overlay, a fingerprint, and a fingerprint sensor according to an embodiment.

FIG. 18 illustrates a system comprising similar elements as FIG. 17. FIG. 18 differs from FIG. 17 in that it does not include a fingerprint sensor surface corresponding to sensor surface 1702 in FIG. 17. In this embodiment, anisotropic conductive material 1705 may act as a protective cover for fingerprint sensor 1701.

In the above embodiments, overlay 1703 may configured to substantially cover and be in direct contact with a screen of device 1700, such as screen 102 in FIG. 1. The screen may comprise a display, a touch screen which is configured to measure and respond to changes in capacitance on and/or between electrodes arranged beneath the surface of the screen, and a fingerprint sensor. Overlay 1700 may protect the screen against harmful environmental and physical factors. Overlay 1700 may allow touch sensors to respond to a touch in areas of the device surface other than the fingerprint sensor but may not allow fingerprint sensor 1701 to accurately image the fingerprint. Conventional overlays such as screen protectors may leave an opening or "cutout" for a fingerprint sensor (including a finger printer sensor surface which protects the fingerprint sensor). However, a cutout may reduce the aesthetic appeal of device 1701 and leave a portion of the screen surface vulnerable to harmful environmental and physical factors. Using the systems of FIGS. 17 and 18, fingerprint sensor 1701 may image the fingerprint through the anisotropic conductive material 1705 fabricated on or inserted into overlay 1703, improving the aesthetic appeal of device 1700 and protecting the screen and fingerprint sensor 1701 against harmful factors. In one embodiment, fingerprint sensor 1701 does not have a fingerprint sensor surface; anisotropic conductive material 1705 protects fingerprint sensor 1701, as illustrated in FIG. 18. The overlay material, including anisotropic conductive material 1705, may be rigid or flexible. In an embodiment, some portions of overlay 1703 may be rigid while some portions may be flexible.

Figure 19:
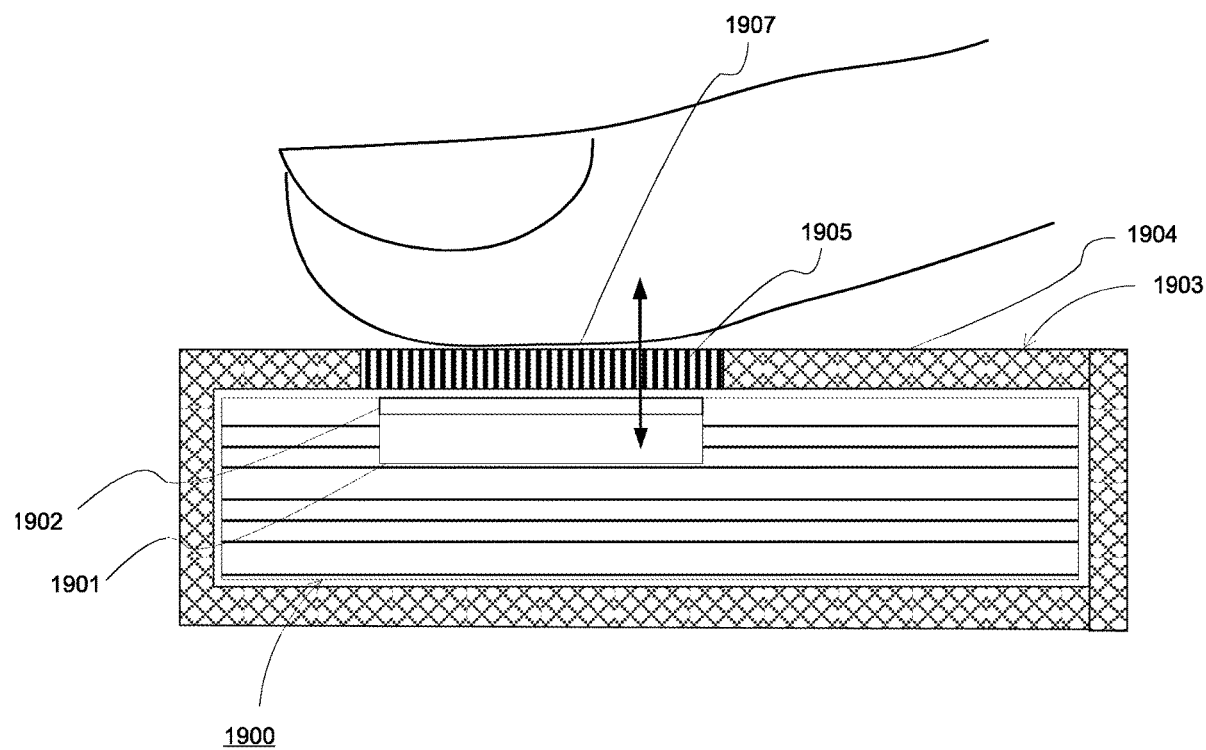
FIG. 19 illustrates a system comprising an enclosure, a fingerprint, and a fingerprint sensor according to an embodiment.

FIG. 19 illustrates elements similar to the elements of FIG. 17. Device 1900 of FIG. 19 differs from device 1700 in FIG. 17 in that device 1900 may be surrounded by enclosure 1903. In an embodiment, enclosure 1903 may completely enclose device 1900. In another embodiment, enclosure 1903 may partially enclose device 1900. Enclosure 1903 may comprise anisotropic conductive material 1905 between finger pad 1907 and fingerprint sensor 1901. The direction of increased conductivity of anisotropic conductive material 1905 is indicated by arrow 1906. Enclosure 1903 may comprise rigid material such as glass, plastic, or ceramic. Enclosure 1903 may comprise flexible material such as film or fabric. Enclosure 1903 may protect the device from harmful environmental factors, such as cold or water, and harmful physical factors, such as impacts, projectile objects, and corrosive chemicals. In various embodiments, Fingerprint sensor 1901 may not include fingerprint sensor 1902 surface; anisotropic conductive material 1905 fabricated on or inserted in enclosure 1903 may act as a protective cover for fingerprint sensor 1901.

In an embodiment, device 1900 of FIG. 19 may comprise a mobile communication device such as a smartphone or cellphone, or a computing device such as a personal digital assistants, smartwatch, mapping device, tablet, or audio player. Enclosure 1903 may comprise a case to protect device 1900 from harmful environmental factors, such as cold or water, and harmful physical factors, such as impacts, projectile objects, and corrosive chemicals.

In a specific embodiment, enclosure 1903 may be directed to use for a mobile communications device or computing device during exercise activity, such as an armband holder or a water resistant case. The computing or mobile communications device may run application software related to the exercise activity, such as mapping software or fitness training software, or software to play an audio program. In an embodiment, device 1900 may be configured to enter a lower power mode after a period of time. The user may want to awaken device 1900 from a lower power mode using the fingerprint sensor in order to interact with the software. In another embodiment, the user may want to activate functions in the software, for example, starting a timer or skipping a song, using the fingerprint sensor in order to interact with the software. Removing device 1900 from enclosure 1903 may be inconvenient to the user and and/or risk damaging the device. Using the system of FIG. 19, fingerprint sensor 1901 may image the fingerprint through anisotropic conducting material 1905 without removing device 1900 from enclosure 1903. In an embodiment, intervening material 1905 may allow touch sensors to respond to a touch in other areas of the device surface other than the fingerprint sensor but may not allow fingerprint sensor 1901 to accurately image the fingerprint.

In an embodiment, device 1900 of FIG. 19 may comprise a computing device such as a notebook computer or tablet computer. Enclosure 1903 may comprise a case to house device 1900 to protect against harmful environmental or physical factors. Using the system of FIG. 19, fingerprint sensor 1901 may image the fingerprint through anisotropic conductive material 1905 without removing device 1900 from enclosure 1903.

In an embodiment, device 1900 of FIG. 19 may comprise an engine-start module for automotive equipment such as cars, trucks, or motorcycles. In a specific embodiment, automotive equipment may comprise a motorcycle or other vehicle with a driver compartment which not enclosed. Enclosure 1903 may comprise a protective film or cover to protect against harmful environmental and physical factors. Using the system of FIG. 19, fingerprint sensor 1901 may image the fingerprint through anisotropic conductive material 1905 without removing device 1900 from enclosure 1903.

In an embodiment device 1900 of FIG. 19 may comprise a control switch for home white goods such as an appliance or security system. In a specific embodiment, white goods may comprise an appliance which uses water, such as a dish or laundry washing machine, and which may incorporate a fingerprint sensor in a control panel that may be exposed to water. Enclosure 1903 may comprise a protective film or cover to protect the control panel against damage or malfunction due to water. Using the system of FIG. 19, fingerprint 1901 sensor may image the fingerprint through anisotropic conductive material 1905 without removing device 1900 from enclosure 1903.

In an embodiment, device 1900 of FIG. 19 may comprise an entry system module such as for home or automotive entry. In a specific embodiment, the entry system module may be exposed to harmful factors such as an outdoor environment or an industrial environment. Enclosure 1903 may comprise a protective film or cover to protect against harmful environmental and physical factors. Using the system of FIG. 19, fingerprint sensor 1901 may image the fingerprint through anisotropic conductive material 1905 without removing device 1900 from enclosure 1903.

Glove and Finger Cot Embodiments

Figure 20:
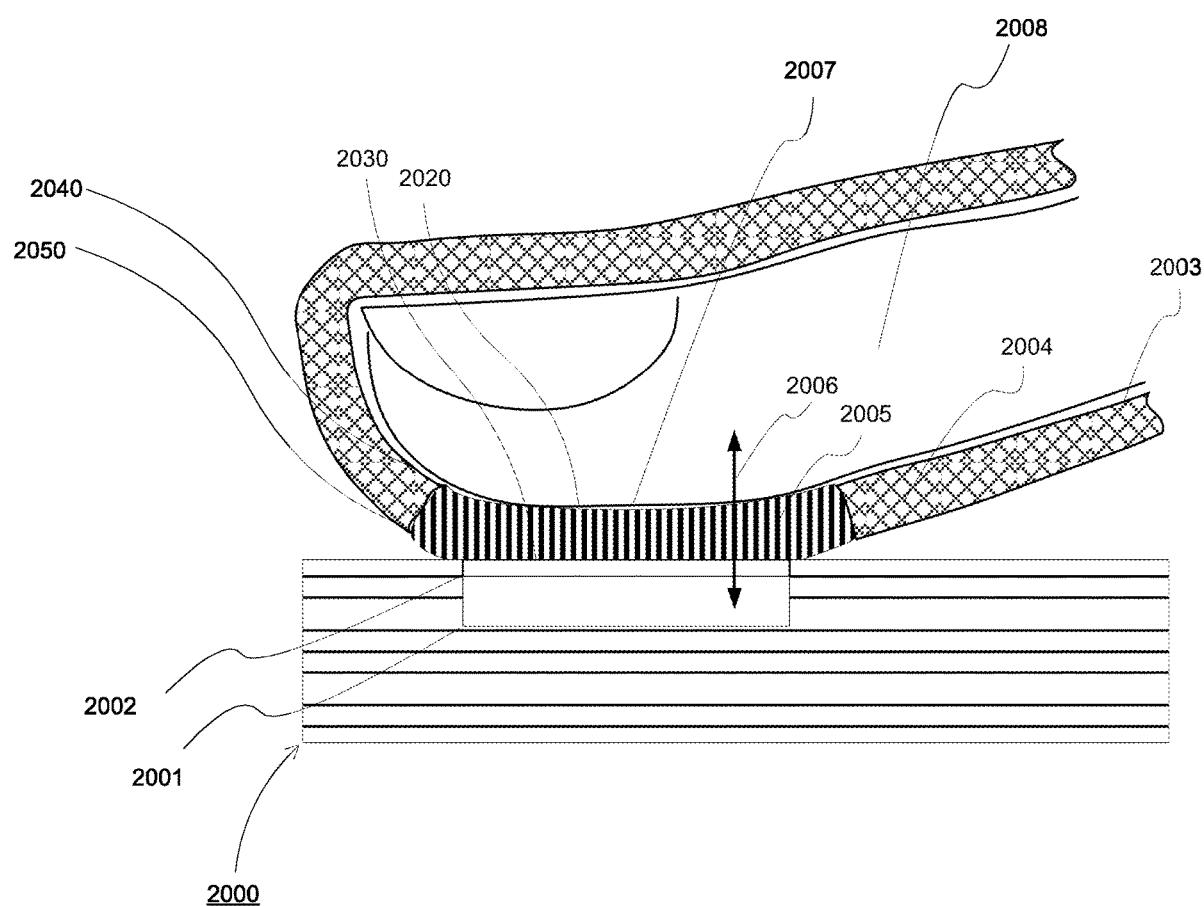
FIG. 20 illustrates a system comprising a glove, a fingerprint, and a fingerprint sensor according to an embodiment.

FIG. 20 illustrates a glove or other hand enclosure 2003 comprising an intervening material 2004, which comprises anisotropic conductive material 2005 disposed between finger pad 2007 of finger 2008 and fingerprint sensor 2001, fingerprint sensor 2001 comprising sensor surface 2002. In an embodiment, anisotropic conductive material 2005 may be fabricated or inserted in intervening material 2004 such that surface 2020 of anisotropic conductive material 2005 is substantially level with surface 2040 of intervening material 2004, and such that surface 2030 of anisotropic conductive material 2005 is substantially level with surface 2050 of intervening material 2004. In another embodiment, surface 2020 of anisotropic conductive material 2005 may be at a substantially different level than surface 2040 of intervening material 2004, and such surface 2030 of anisotropic conductive material 2005 may be at a substantially different level than surface 2050 of intervening material 2004. In another embodiment, anisotropic conductive material 2005 may be surrounded by intervening material 2004. The direction of increased conductivity 2006 of the anisotropic conductive material 2005 is substantially orthogonal to surface 2020 and 2030 is indicated by arrow 2006.

As illustrated in FIGS. 2 and 3, device 2000 may include a fingerprint controller (not shown), which may be configured to convert measured capacitance of fingerprint sensor 2001 into fingerprint data. Device 2000 may comprise a processor (not processor) which may further process fingerprint data or store fingerprint data in a memory. Device 2000 may comprise a memory (not shown) to store fingerprint data. In other embodiments, device 2000 may be configured to communicate with a controller, processor, or memory located in another device.

Figure 21:
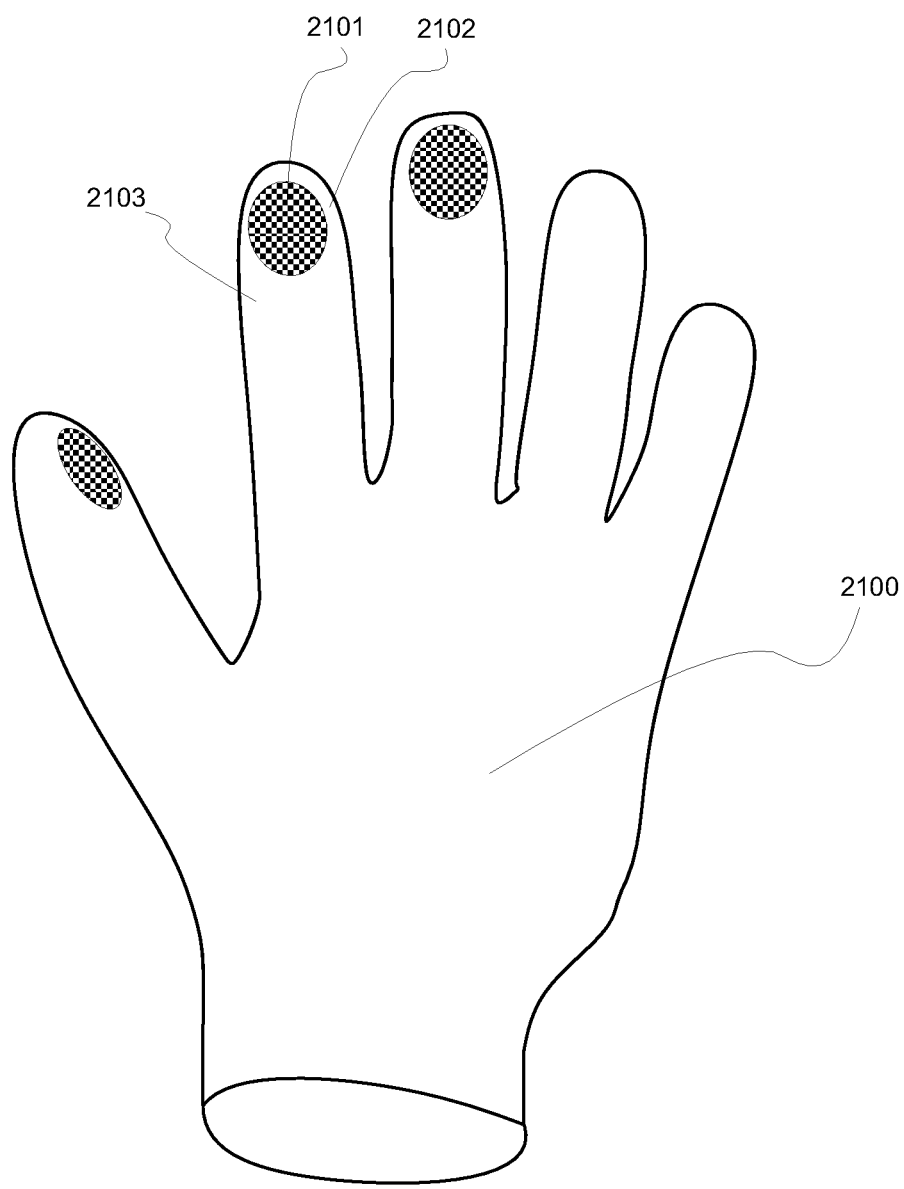
FIG. 21 illustrates a glove comprising anisotropic conductive material according to an embodiment.

FIG. 21 illustrates a glove 2100 comprising anisotropic conductive material 2101 fabricated or inserted in the glove material in the fingertip areas 2102 corresponding to the location of a finger pad (1607 of FIG. 20) on a finger 2103. As illustrated in FIGS. 20 and 21, anisotropic conductive material 2101 may be fabricated or inserted as patches in glove 2100 such that the direction of conductivity is perpendicular to the surface of finger pad 2007. When finger 2008 or 2103 applies fingertip 2102 of glove 2100 to fingerprint sensor 2001, anisotropic conductive material 2101 may contact both finger pad 2007 and fingerprint sensor surface 2002, enabling fingerprint sensor 2001 to accurately image the fingerprint. In an embodiment, the patches may be approximately the size of a finger pad. Anisotropic conductive material 2005 may be flexible at the geometry of a finger (i.e. can conform to the curvature of a finger) but rigid enough that its surface is not deformed by the fingerprint ridge/valley structure.

In one embodiment, glove 2100 may be directed to use for exercise activity, such as running, hiking, skiing, etc. Glove 2100 may be designed to protect the hand from harmful or uncomfortable environmental factors, such as wet and cold, or harmful or uncomfortable physical factors such as cuts or impacts. The device may be a computing device configured to run application software related to the exercise activity, such as mapping software or fitness training software, or the computing device may run software to play an audio program. In an embodiment, the device may be configured to enter a lower power mode after a period of time. The user may want wake the device from lower power mode using the fingerprint sensor to interact with device software. In another embodiment, the user may want to activate functions in the software, for example, starting a timer or skipping a song, using the fingerprint sensor in order to interact with the software. Removing glove 2100 may be inconvenient and possibly harmful to the user. Using the system of FIG. 20 and FIG. 21, fingerprint sensor 2001 may image the fingerprint through anisotropic conducting material 2101 fabricated on or inserted in the glove 2100. In an embodiment, intervening material 2003 may allow conventional touch sensors to respond to a touch in other areas of the device surface.

In an embodiment, glove 2100 may be directed to use for in an industrial environment. Glove 2100 may be designed to protect the hand from harmful or uncomfortable environmental factors, such as wet, cold or heat, or dangerous chemicals or gases, or harmful or uncomfortable physical factors such as cuts or impacts. Using the system of FIGS. 20 and 21, the fingerprint sensor 2001 may image the fingerprint from finger pad 2007 through anisotropic conducting material 2101 fabricated on or inserted in glove 2100.

In an embodiment, glove 2100 may be directed to use in an outdoor environment. In an embodiment, glove 2100 may be worn by a user attempting to start automotive equipment comprising a motorcycle or other vehicle with a driver compartment which not enclosed. In another embodiment, glove 2100 may be may be worn by a user attempting to gain access to a building or automobile, for example. In such cases, glove 2100 may be designed to protect the hand from harmful or uncomfortable environmental factors, such as wet, cold, or heat, or harmful or uncomfortable physical factors such as cuts or impacts. Using the system of FIGS. 20 and 21, fingerprint sensor 2001 may image the fingerprint from finger pad 2007 through anisotropic conducting material 2101 fabricated or inserted in the glove.

In an embodiment, a glove may be directed to use in a medical environment. The glove may be designed to protect the hand from harmful or uncomfortable environmental factors, such as wet, cold, or heat, or harmful physical factors such as cuts, impacts, or bodily fluids. Using the system of FIGS. 20 and 21, fingerprint sensor 2001 may image the fingerprint from finger pad 2007 through anisotropic conducting material 2101 fabricated or inserted in the glove.

Figure 22:
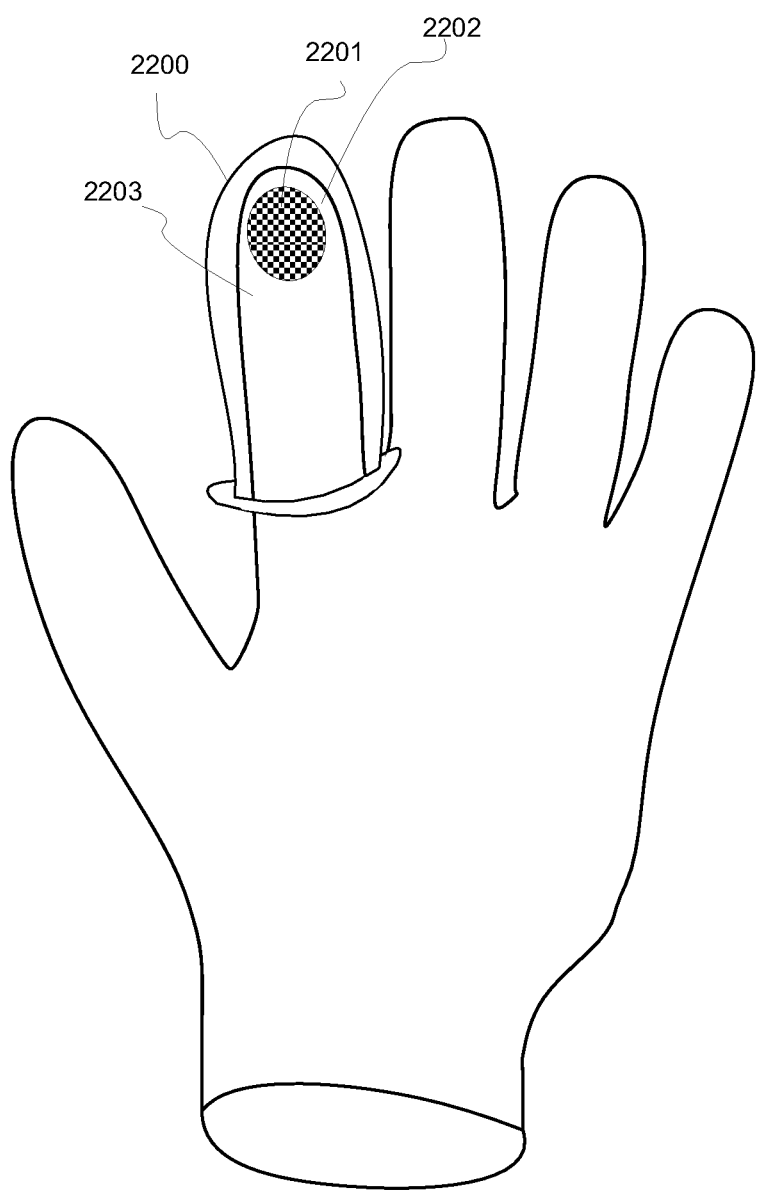
FIG. 22 illustrates a finger cot comprising anisotropic conductive material according to an embodiment.

In all of the above embodiments, the hand enclosure could comprise a finger cot or other finger enclosure, as illustrated in FIG. 22. In an embodiment, finger cot 2200 comprises anisotropic conductive material 2201 fabricated or inserted in fingertip area 2202 corresponding to the location of finger pad (1607 of FIG. 20) on finger 2203 inserted in finger cot 2200. As illustrated in FIGS. 20 and 22, anisotropic conductive material 2201 may be fabricated or inserted as patches in finger cot 2200 such that the direction of conductivity is perpendicular to the surface of finger pad 2007.

When finger 2203 applies fingertip 2202 of finger cot 2200 to fingerprint sensor 2001, anisotropic conductive material 2201 contacts both finger pad 2007 and fingerprint sensor 2001, enabling fingerprint sensor 2001 to accurately image the fingerprint. In an embodiment, the patches may be approximately the size of a finger pad. Anisotropic conductive material 2201 may be flexible at the geometry of a finger, but rigid enough that its surface is not deformed by the fingerprint ridge/valley structure.

In an embodiment, finger cot 2200 may be directed to use during recreational activity, such as fly fishing or sewing. In an embodiment, finger cot 2200 may be directed to use in a medical environment. Finger cot 2200 may be designed to protect the finger harmful or uncomfortable physical factors such as cuts or jabs.

In the above description, numerous details are set forth. It will be apparent, however, to one of ordinary skill in the art having the benefit of this disclosure, that embodiments of the present invention may be practiced without these specific details. In some instances, well-known structures and devices are shown in block diagram form, rather than in detail, in order to avoid obscuring the description.

Some portions of the detailed description are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared and otherwise manipulated. It has proven convenient at times, principally for reasons of common usage, to refer to these signals as bits, values, elements, symbols, characters, terms, numbers or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "integrating," "comparing," "balancing," "measuring," "performing," "accumulating," "controlling," "converting," "accumulating," "sampling," "storing," "coupling," "varying," "buffering," "applying," or the like, refer to the actions and processes of a computing system, or similar electronic computing device, that manipulates and transforms data represented as physical (e.g., electronic) quantities within the computing system's registers and memories into other data similarly represented as physical quantities within the computing system memories or registers or other such information storage, transmission or display devices.

The words "example" or "exemplary" are used herein to mean serving as an example, instance or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or." That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such.

Embodiments described herein may also relate to an apparatus for performing the operations herein. This apparatus may be specially constructed for the required purposes, or it may comprise a general-purpose computer selectively activated or reconfigured by a computer program stored in the computer. Such a computer program may be stored in a non-transitory computer-readable storage medium, such as, but not limited to, any type of disk including floppy disks, optical disks, CD-ROMs and magnetic-optical disks, read-only memories (ROMs), random access memories (RAMs), EPROMs, EEPROMs, magnetic or optical cards, flash memory, or any type of media suitable for storing electronic instructions. The term "computer-readable storage medium" should be taken to include a single medium or multiple media (e.g., a centralized or distributed database and/or associated caches and servers) that store one or more sets of instructions. The term "computer-readable medium" shall also be taken to include any medium that is capable of storing, encoding or carrying a set of instructions for execution by the machine and that causes the machine to perform any one or more of the methodologies of the present embodiments. The term "computer-readable storage medium" shall accordingly be taken to include, but not be limited to, solid-state memories, optical media, magnetic media, any medium that is capable of storing a set of instructions for execution by the machine and that causes the machine to perform any one or more of the methodologies of the present embodiments.

The algorithms and circuits presented herein are not inherently related to any particular computer or other apparatus. Various general-purpose systems may be used with programs in accordance with the teachings herein, or it may prove convenient to construct a more specialized apparatus to perform the required method steps. The required structure for a variety of these systems will appear from the description below. In addition, the present embodiments are not described with reference to any particular programming language. It will be appreciated that a variety of programming languages may be used to implement the teachings of the embodiments as described herein.

The above description sets forth numerous specific details such as examples of specific systems, components, methods and so forth, in order to provide a good understanding of several embodiments of the present invention. It will be apparent to one skilled in the art, however, that at least some embodiments of the present invention may be practiced without these specific details. In other instances, well-known components or methods are not described in detail or are presented in simple block diagram format in order to avoid unnecessarily obscuring the present invention. Thus, the specific details set forth above are merely exemplary. Particular implementations may vary from these exemplary details and still be contemplated to be within the scope of the present invention.

It is to be understood that the above description is intended to be illustrative and not restrictive. Many other embodiments will be apparent to those of skill in the art upon reading and understanding the above description. The scope of the invention should, therefore, be determined with reference to the appended claims, along with the full scope of equivalents to which such claims are entitled.

What is claimed is:

1. A capacitance sensing-compatible overlay comprising conductive elements disposed in a first portion of material such that the conductive elements are aligned orthogonal to a first surface of the material and a second surface of the material,
wherein a first conductivity in the orthogonal to the first and second surfaces is greater than a second conductivity parallel to at least one of the first and second surfaces,
wherein the conductive elements are distributed within the overlay asymmetrically with measurement electrodes for a capacitance measurement circuit.

2. The overlay of claim 1, wherein the first conductivity is substantially constant.

3. The overlay of claim 1, wherein the material is rigid.

4. The overlay of claim 1, further comprising a second portion of material disposed over the first surface.

5. The overlay of claim 4, wherein the second portion of material comprises conductive elements disposed in the second portion such that the conductive elements are aligned in the first direction, and wherein the second portion has a third conductivity in the first direction greater than a fourth conductivity in at least one other direction.

6. A method comprising:
forming a plurality of conductive elements over a plurality of measurement electrodes for a capacitance measurement device;
wherein the plurality of conductive elements is disposed between a first surface and a second surface, and orthogonal to the second surface at a point at which a conductive object is disposed,
wherein the conductive elements are distributed asymmetrically with the plurality of the measurement electrodes, and
wherein a first conductivity created by the plurality of conductive elements is substantially greater than a second conductivity created by the plurality of conductive elements, the first conductivity substantially orthogonal to the first surface.

7. The method of claim 6, wherein the plurality of conductive elements are formed in a rigid material.

8. The method of claim 6, wherein the plurality of conductive elements are disposed to align with the plurality of measurement electrodes for the capacitance measurement device.

9. The method of claim 6, wherein the plurality of conductive elements are disposed such that they are unaligned with the plurality of measurement electrodes for the capacitance measurement device.

10. The method of claim 6, wherein the first surface is disposed proximate to the plurality of measurement electrodes.

11. The method of claim 6, wherein the second surface is disposed proximate to at least one feature of a fingerprint.

12. An overlay comprising:
a first surface disposed proximate to a plurality of capacitance measurement electrodes;
a second surface configured to provide a point of contact for a conductive object; and
a material disposed between the first surface and the second surface, the material comprising conductive elements disposed in the material such that the conductive elements are aligned in a first direction from the first surface to the second surface, wherein a first conductivity in the first direction is greater than a second conductivity in at least one other direction, the at least one other direction parallel to at least the first or second surface, wherein the conductive elements are distributed within the material asymmetrically with measurement electrodes for a plurality of capacitance sensor cells.

13. The overlay of claim 12, wherein the first conductivity is substantially constant.

14. The overlay of claim 12, wherein the first direction is substantially orthogonal to the second surface at a point which the conductive object is disposed.

15. The overlay of claim 12, wherein the conductive elements correspond to measurement electrodes for the plurality of capacitance sensor cells.

16. The overlay of claim 12, wherein the conductive elements are in physical contact with at least one of the first surface and the second surface.

* * * * *